(12) United States Patent
Katsuhara et al.

(10) Patent No.: US 9,155,524 B2
(45) Date of Patent: Oct. 13, 2015

(54) PHYSIOLOGICALLY ACTIVE SUBSTANCE COLLECTING DEVICE AND BIOLOGICAL INFORMATION ACQUISITION METHOD

(75) Inventors: Tomoko Katsuhara, Kanagawa (JP); Yuuki Watanabe, Kanagawa (JP); Masahiro Matsumoto, Kanagawa (JP)

(73) Assignee: Sony Corporation, Tokyo (JP)

( * ) Notice: Subject to any disclaimer, the term of this patent is extended or adjusted under 35 U.S.C. 154(b) by 1098 days.

(21) Appl. No.: 13/207,969

(22) Filed: Aug. 11, 2011

(65) Prior Publication Data

US 2012/0058496 A1    Mar. 8, 2012

(30) Foreign Application Priority Data

Aug. 18, 2010    (JP) ................ P2010-183121

(51) Int. Cl.
```
A61B 10/00      (2006.01)
A61B 5/145      (2006.01)
B01L 3/00       (2006.01)
G01N 35/00      (2006.01)
G01N 1/38       (2006.01)
G01N 30/88      (2006.01)
```

(52) U.S. Cl.
CPC ......... *A61B 10/0064* (2013.01); *A61B 5/14517* (2013.01); *B01L 3/502715* (2013.01); *G01N 35/00009* (2013.01); *G01N 2001/383* (2013.01); *G01N 2030/8813* (2013.01)

(58) Field of Classification Search
None
See application file for complete search history.

(56) References Cited

U.S. PATENT DOCUMENTS

| | | | | |
|---|---|---|---|---|
| 5,126,025 A | * | 6/1992 | Carson et al. ................. | 204/451 |
| 2003/0125671 A1 | * | 7/2003 | Aramata et al. .............. | 604/236 |
| 2010/0132485 A1 | * | 6/2010 | Erez et al. .................. | 73/863.11 |

FOREIGN PATENT DOCUMENTS

| | | |
|---|---|---|
| JP | 2582957 | 11/1996 |
| JP | 11-38004 | 2/1999 |
| JP | 2000-131318 | 5/2000 |
| JP | 2006-94969 | 4/2006 |

* cited by examiner

*Primary Examiner* — Chris L Chin
*Assistant Examiner* — Richard Moerschell
(74) *Attorney, Agent, or Firm* — Sony Corporation

(57) ABSTRACT

A physiologically active substance collecting device, includes: a collecting section brought into contact with a body surface of a living organism to acquire a physiologically active substance from the body surface; and a liquid sending means for sending a solvent to the collecting section, the collecting section having an aperture at which the solvent flown by being sent from the liquid sending means contacts the body surface.

5 Claims, 15 Drawing Sheets

◆DAY1,■DAY2,▲DAY3,●DAY4

PHYSIOLOGICALLY ACTIVE SUBSTANCE COLLECTING DEVICE AND BIOLOGICAL INFORMATION ACQUISITION METHOD

CROSS REFERENCES TO RELATED APPLICATIONS

The present application claims priority to Japanese Priority Patent Application JP 2010-183121 filed in the Japan Patent Office on Aug. 18, 2010, the entire content of which is hereby incorporated by reference.

BACKGROUND

The present application relates to physiologically active substance collecting devices and biological information acquisition methods, specifically to physiologically active substance collecting devices used to acquire physiologically active substances from the body surface of a living organism.

Known methods of acquiring information concerning stress, emotion, menstrual cycle, and other conditions of a living organism (hereinafter, "information concerning a living organism" or, simply, "biological information") include biological information acquisition methods that are based on psychological evaluations involving, for example, questioning and sensory questionnaires, physiological tests measuring, for example, brain waves or myoelectricity, and behavior measurements involving the use of, for example, a work record. For example, JP-A-2006-94969 (Patent Document 1) discloses a technique that determines the menstrual cycle based on heart rates. Japanese Patent No. 2582957 (Patent Document 2) discloses a life activity monitoring system that monitors body temperature fluctuations and heart rates.

In recent years, simpler techniques have been developed that acquire information concerning a living organism with the use of a physiologically active substance contained in blood, urine, or saliva as an index. For example, JP-A-11-38004 (Patent Document 3) discloses a method for quantifying stress using the concentration of adrenal cortical steroid and/or its metabolic products in saliva as an index. JP-A-2000-131318 (Patent Document 4) discloses a method that allows the stress level to be grasped as either "comfortable" or "uncomfortable" using biological substances such as β-endorphin, dopamine, immunoglobulin A, and prostaglandin D2 contained in blood or in other body parts as an index.

SUMMARY

The biological information acquisition methods in which the physiologically active substances contained in blood, urine, or saliva are used as an index are advantageous, because these methods are simpler than methods involving psychological evaluations, physiological tests, or behavior measurements, and do not require large devices.

On the other hand, the methods require the procedure of collecting blood, urine, and saliva for the quantification of physiologically active substances. For example, when blood is used, blood collection can be mentally or physically demanding to a subject. The mental and physical load associated with blood collection may itself be perceived as stress, and may cause changes in the subject's conditions, including stress and emotion, and prevent accurate acquisition of biological information.

Use of urine and saliva can circumvent the problematic medical practice issue raised in blood collection, and can reduce the mental and physical load put on the subject. It is, however, difficult to collect urine and saliva over a time course or on a steady basis, and, because there is a time lag between the collection of urine or saliva and the body's metabolism of the physiologically active substance contained in urine or saliva, it is difficult to acquire biological information in real-time. Further, even though urine or saliva collection does not produce as much mental or physical load as blood collection, it still makes the subject strongly aware of the collection procedure, presenting difficulties in the accurate acquisition of biological information.

Accordingly, there is a need for a physiologically active substance collecting device that can be used to collect physiologically active substances from a living organism on a steady basis in a convenient and minimally invasive manner.

According to an embodiment of the present disclosure, there is provided a physiologically active substance collecting device that includes: a collecting section brought into contact with a body surface of a living organism to acquire a physiologically active substance from the body surface; and a liquid sending means for sending a solvent to the collecting section, the collecting section having an aperture at which the solvent flown by being sent from the liquid sending means contacts the body surface. In the physiologically active substance collecting device, the solvent is contacted to the body surface of a living organism at the collecting section to enable the collection of the physiologically active substance into the solvent.

The physiologically active substance collecting device may further include: a lead-out section that drains the solvent contacted the body surface at the aperture; and a supplying means with which an absorber that absorbs and holds the solvent is sent to the lead-out section. In this way, the physiologically active substance collecting device can preserve the physiologically active substance-containing solvent in the state of being absorbed and held by the absorber after the solvent has contacted the body surface of the living organism at the collecting section. The supplying means may be adapted to send the absorber to the lead-out section by rotating a core and reeling out the absorber wound around the core. The physiologically active substance collecting device may further include a drying unit that evaporates and removes the solvent from the absorber absorbing and holding the solvent.

The physiologically active substance collecting device may further include an air sending unit that sends air to the collecting section to selectively introduce the solvent and air into the collecting section. By selectively introducing the solvent and air into the collecting section, the solvent that comes into contact with the body surface of a living organism at the collecting section can be collected in a flow separated by air in predetermined volumes.

It is desirable in the physiologically active substance collecting device that the collecting section include a substrate that includes a channel that flows the solvent, a solvent inlet for the channel, a solvent outlet for the channel, and the aperture positioned between the inlet and the outlet of the channel, and that the substrate is replaceable from the collecting section.

The physiologically active substance collecting device may further include: a quantifying section that quantifies the physiologically active substance; and a determining section that automatically determines and acquires information concerning the living organism based on the quantified value of the physiologically active sub stance.

Here, the physiologically active substance may be, for example, cortisol, monoamine, estrogen, or growth hormone. In this way, the information concerning the stress, emotion, menstrual cycle, exercise effect in the living organism can be acquired as the information.

As used herein, "information concerning a living organism" encompasses not only information concerning, for example, stress, emotion, menstrual cycle, and exercise effect, but information concerning sleepiness (wakefulness level), health condition, and circadian rhythm (biological rhythm). The meaning of "emotion" encompasses, for example, excitement, fear, anger, aggression, comfort, and anxiety.

The "physiologically active substance" includes a wide range of substances present in a living organism, and that have physiological effects and pharmacological effects on the living organism to take part in changes in the state of a living organism, including stress, emotion, menstrual cycle, and metabolism. Specific examples of the physiologically active substance include steroid hormones such as cortisol and estradiol, catecholamines such as adrenaline and dopamine, and physiologically active peptides such as oxytocin and endorphin (see Table 1 below).

The physiologically active substance collecting device according to the embodiment of the present disclosure can thus be used to collect physiologically active substances from a living organism on a steady basis in a convenient and minimally invasive manner.

Additional features and advantages are described herein, and will be apparent from the following Detailed Description and the figures.

DETAILED DESCRIPTION

Embodiments of the present application will be described below in detail with reference to the drawings.

It should be noted that the embodiment below is merely an illustrative representation of the present disclosure, and should not be construed to narrow the scope of the present disclosure. Descriptions will be given in the following order.

1. Physiologically Active Substance Collecting Device According to First Embodiment of the Present Disclosure
   (1) Overview
   (2) Overall configuration
   (3) Collecting section
   (4) Supplying unit
2. Physiologically Active Substance Collecting Device According to Variations of First Embodiment
   (1) First Variation
   (2) Second Variation
   (3) Third Variation
3. Biological Information Acquisition Method
   (1) Extraction of Physiologically Active Substance
   (2) Quantification of Physiologically Active Substance
   (3) Acquisition of Biological Information 1. Physiologically Active Substance Collecting Device According to First Embodiment of the Present Disclosure (1) Overview For the accurate sensing of biological information, the present inventors conducted intensive studies on techniques for collecting physiologically active substances from a living organism. The inventors found, for the first time, that physiologically active substances could be acquired from body surfaces such as finger and palm surfaces, as will be described in detail later in Examples.

It is common practice to acquire physiologically active substances from bodily fluids such as blood, urine, and saliva. To the knowledge of the present inventors, there is no report of acquiring physiologically active substances from the body surface of a living organism.

The detailed mechanism by which physiologically active substances are acquired from the body surface remains elusive. However, there is a possibility that the physiologically active substance secreted into, for example, sweat and sebum may be present on the body surface. There is another possibility that the physiologically active substance in blood passes through body surface cells to reach the body surface. Because many of the physiologically active substances are soluble in lipid and permeable through cell membrane, it is highly probable that the physiologically active substance acquired from the body surface is one that is secreted into sebum or that has passed through the cells.

The present disclosure has been made based on these new findings, by recognizing the need for a physiologically active substance collecting device that can be used to acquire physiologically active substances from the body surface of a living organism.

(2) Overall Configuration

Figure 1:
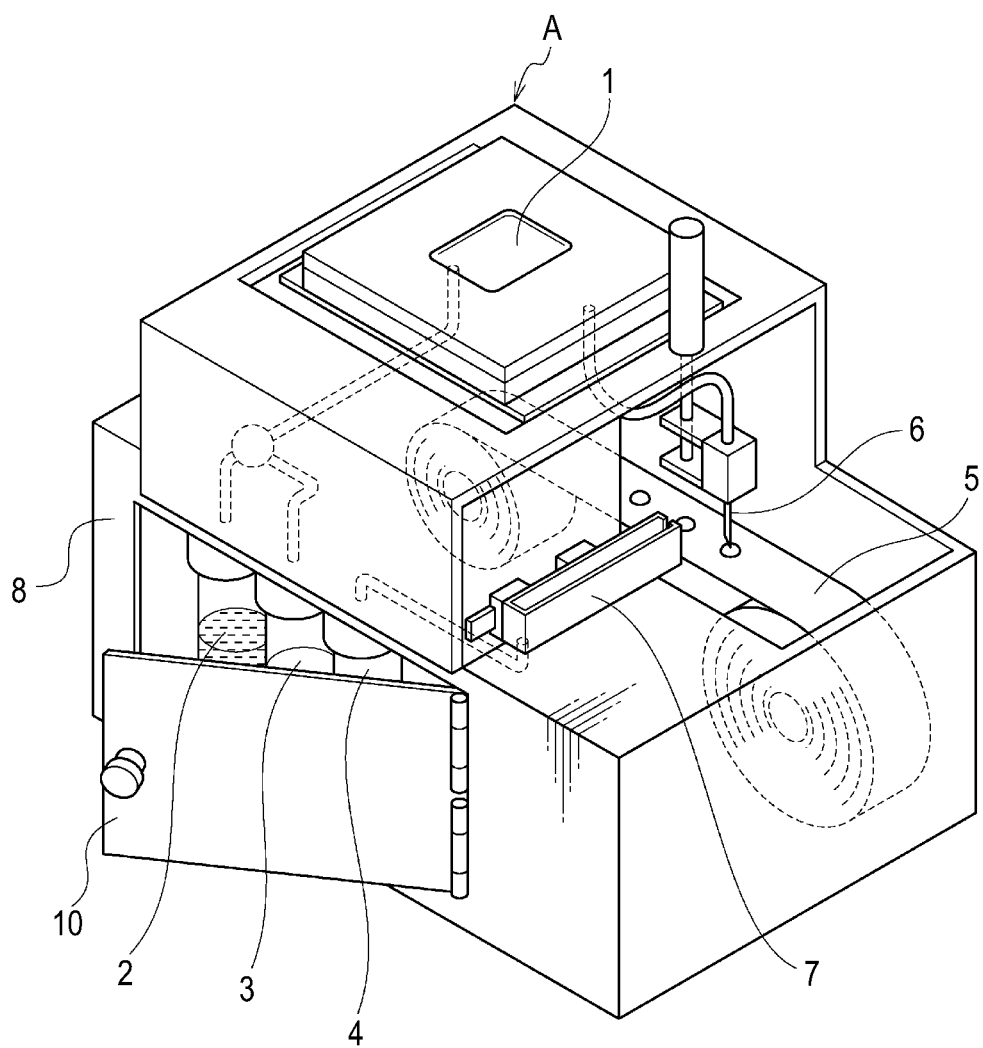
FIG. 1 is a perspective view explaining the schematic structure of a physiologically active substance collecting device according to First Embodiment of the present disclosure.
Figure 2:
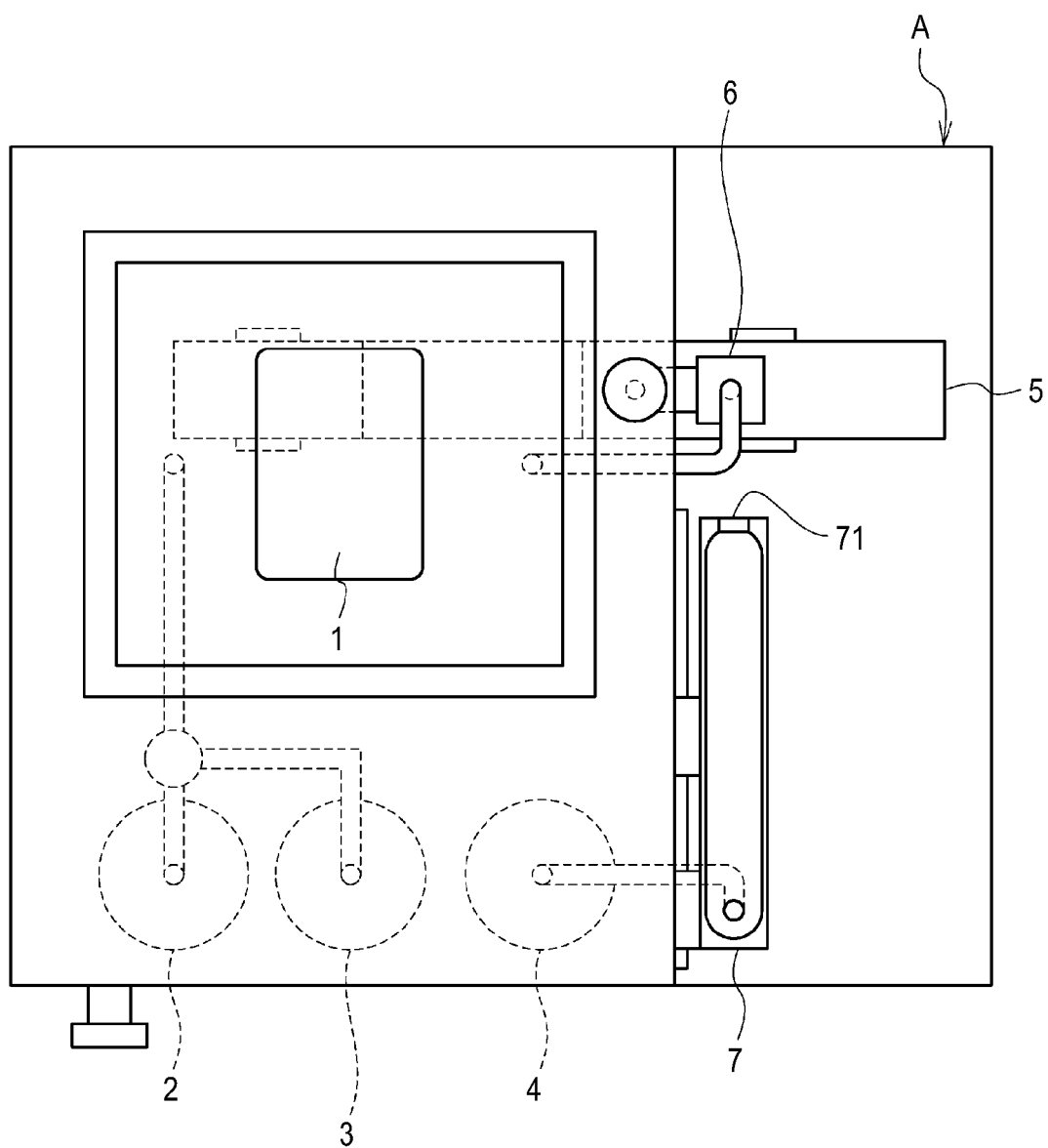
FIG. 2 is a top view explaining the schematic structure of the physiologically active substance collecting device according to First Embodiment of the present disclosure.

FIG. 1 and FIG. 2 are perspective views explaining the schematic structure of a physiologically active substance collecting device according to First Embodiment of the present disclosure. FIG. 1 represents a perspective view. FIG. 2 represents a top view.

In FIG. 1, a physiologically active substance collecting device A is configured to include a collecting section 1 brought into contact with the surface of a living organism (hereinafter, also referred to as "body surface") to acquire a physiologically active substance from the body surface, a liquid sending unit that sends a solvent to the collecting section 1, an air sending unit that sends air to the collecting section 1, and a lead-out section 6 that drains the solvent that has contacted the body surface at the collecting section 1. The solvent may be water or various organic solvents. For example, ethanol water can be used.

In FIG. 1, a solvent tank 2 is provided as a component of the liquid sending unit. In addition to the solvent tank 2, the liquid sending unit is also configured from other components such as pumps, tubes, and valves used to send the solvent inside the solvent tank 2 to the collecting section 1. An air tank 3 is provided as a component of the air sending unit. In addition to the air tank 3, the air sending unit is also configured from other components such as pumps, tubes, and valves used to send air inside the air tank 3 to the collecting section 1. The air tank 3 serves as a filter that prevents dust and foreign particles from being sucked into the tubes or valves.

The lead-out section 6 is tubular in shape, and configured so that the solvent sent from the collecting section 1 after contacted the body surface can be drained through the hole at one end. The lead-out section 6 functions to lead out the solvent to an absorber 5 disposed underneath, and drops the solvent onto the absorber 5 either intermittently or continuously. The absorber 5 may be made of material that can absorb the solvent. For example, the absorber 5 may be formed as a filer paper, or a film of carriers such as agarose gel, sepharose gel, silica gel, and alumina gel, or even a film of such carriers formed on a metallic or polymeric base.

Figure 3:
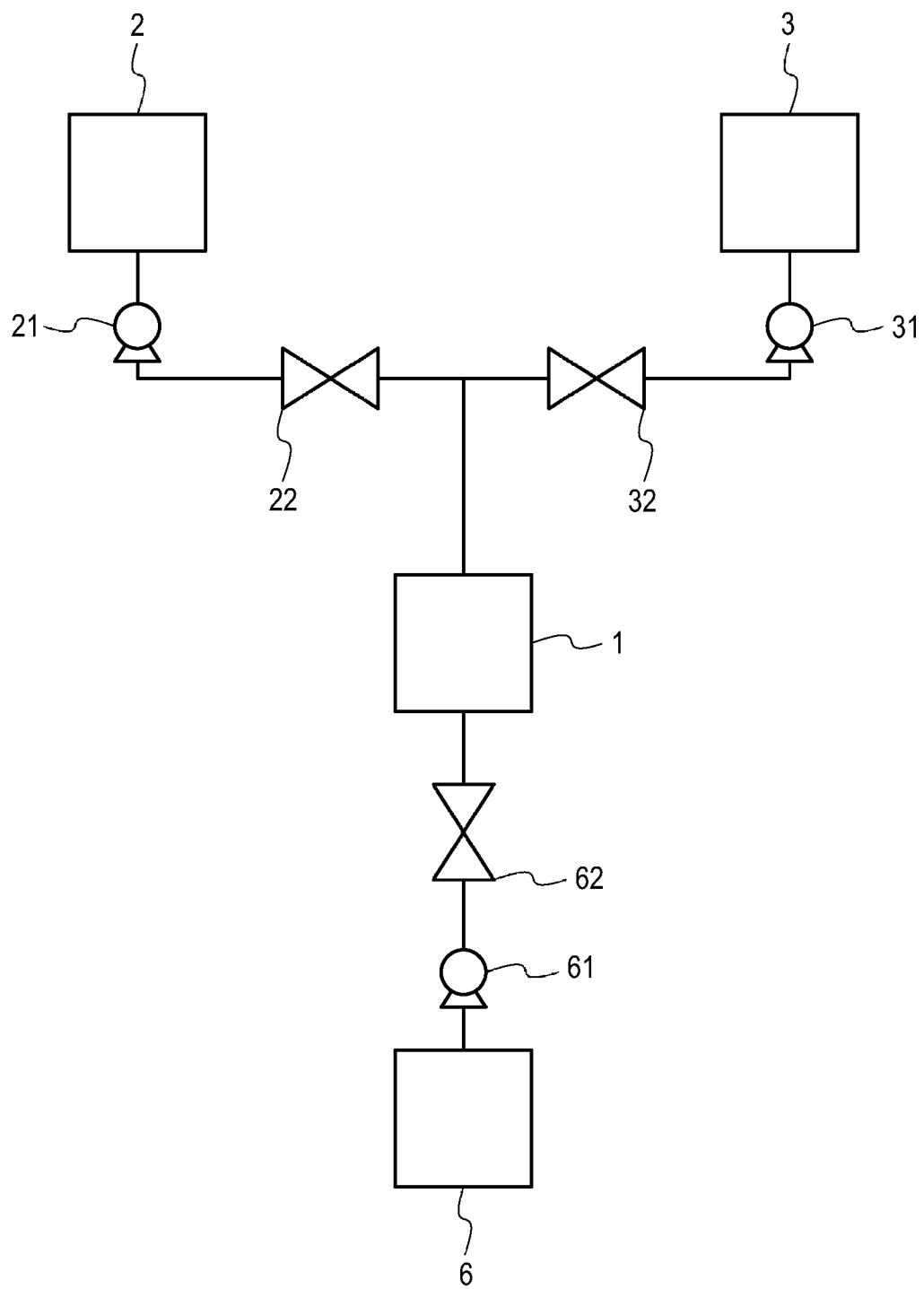
FIG. 3 is a block diagram explaining a flow of a solvent in the physiologically active substance collecting device.

FIG. 3 is a block diagram representing a flow of the solvent in the physiologically active substance collecting device A.

The collecting section 1 is connected to a channel used to send liquid from the solvent tank 2. The collecting section 1 is also connected to a channel used to send air from the air tank 3. The collecting section 1 is also connected to a channel through which the solvent contacted the body surface, and air are sent to the lead-out section 6. General-purpose tubes can be used for these channels. A general-purpose pump (pumps 21, 31, 61) is provided for each channel to sent liquid or air.

The tube connecting the solvent tank 2 to the collecting section 1, and the tube connecting the air tank 3 to the collecting section 1 merge on the upstream side of the collecting section 1. Referring to the figure, valves 22 and 32 are provided on the way to the junction from the solvent tank 2 and the air tank 3. In the physiologically active substance collecting device A, the valves 22 and 32 are opened and closed under the control of a system control unit (not illustrated) to selectively introduce the solvent and air to the collecting section 1. In the figure, a valve 62 is provided for the tube that connects the collecting section 1 to the lead-out section 6. The valve 62 is opened and closed under the control of the system control unit, and serves to start and stop the draining of the solvent from the lead-out section 6. The system control unit is provided inside a control box 8 illustrated in FIG. 1.

In the physiologically active substance collecting device A, it is preferable that the tubes, valves, and pumps through which the solvent is flown be made of material that does not easily attract the physiologically active substance, or be subjected to a surface treatment that makes the adsorption of the physiologically active substance difficult.

Referring back to FIG. 1 and FIG. 2, a waste liquid receptor 7 (hereinafter, "waste liquid tray 7") is provided that accepts the solvent drained through the hole of the lead-out section 6. The solvent collected in the waste liquid tray 7 is sent to the waste liquid tank 4 and stored therein. As illustrated in the figures, the lead-out section 6 is movable between the solvent drain position for the absorber 5 and the solution drain position for the waste liquid tray 7. A driving unit that moves the lead-out section 6 is realized by using known components, for example, such as a holder, a feed screw, a guide, and a motor.

Referring to FIG. 2, the waste liquid tray 7 has a notch 71 that provides a passage way for the movement of the lead-out section 6. The notch 71 is formed by cutting out a part of the side wall of the waste liquid tray 7 on the side of the lead-out section 6 in a width greater than the thickness of the lead-out section 6. The provision of the notch 71 allows the lead-out section 6 to move between the solvent drain position for the absorber 5 and the solution drain position for the waste liquid tray 7 only by moving in the horizontal direction.

The absorber 5 is stored by being wound around a core. By the rotation of the core, the absorber 5 is reeled out to underneath the lead-out section 6 assuming the solvent drain position. As the absorber 5 is sent out, the lead-out section 6 drops the solvent onto the absorber 5 either intermittently or continuously, and the sample is held on the absorber 5 (will be described in detail later with reference to FIG. 7). Note that, as used herein, the "sample" means a solvent that has contacted the body surface and contains a biological substance, and encompasses solvents collected for comparison without being contacted with the body surface.

Because the sample is collected by being absorbed and held on the absorber 5, the biological substance in the sample can be preserved more stably than in the method in which the sample is collected in the form of a solution in a container such as a tube. Further, the device configuration can be simplified for the miniaturization of the device.

Referring to the figure, a lower cover 10 is opened and closed to replace the solvent tank 2, the air tank 3, and the waste liquid tank 4.

(3) Collecting Section

Figure 4A:
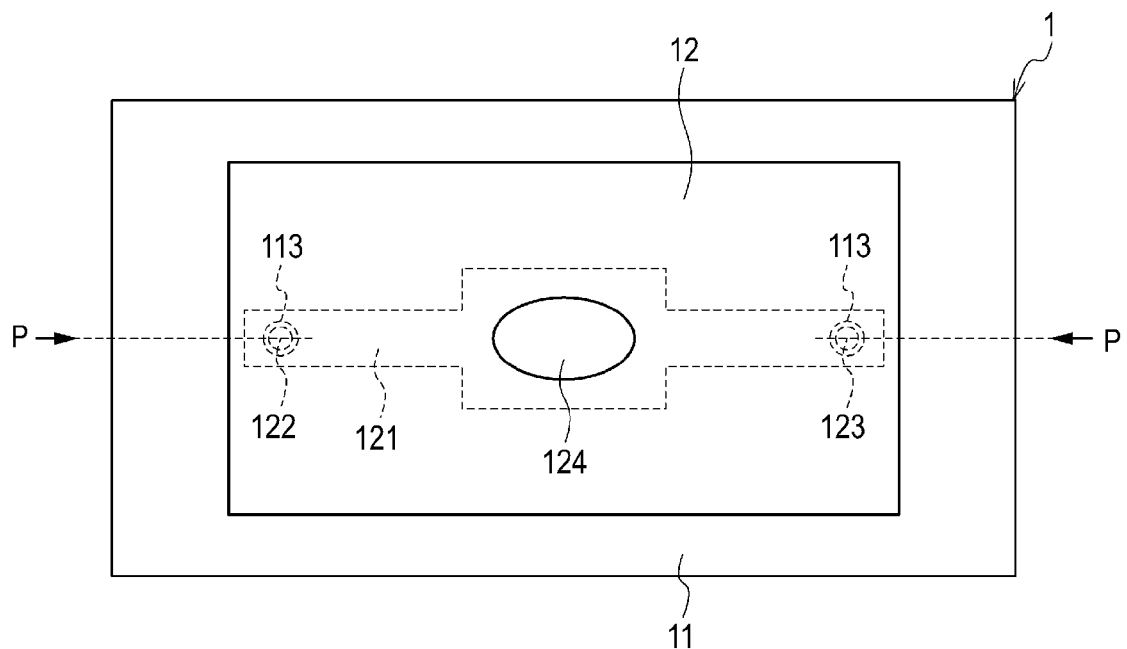
FIGS. 4A and 4B are schematic views explaining the configuration of a collecting section.
Figure 4B:
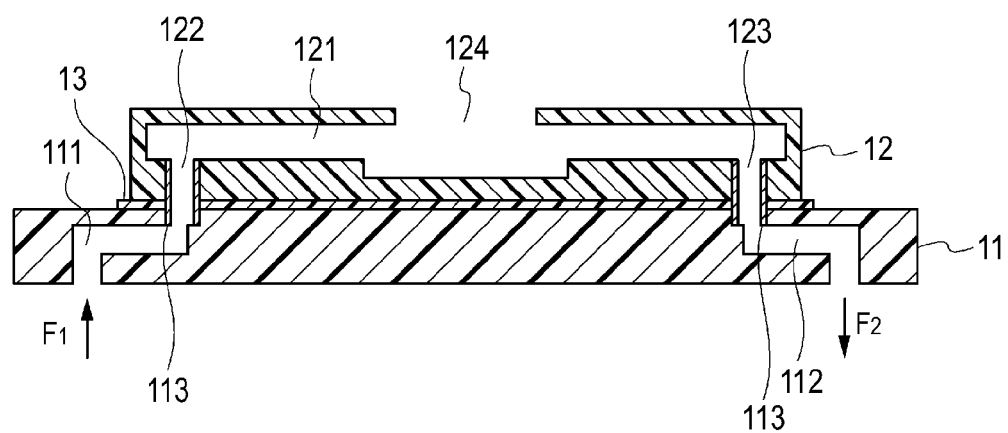
Figure 5:
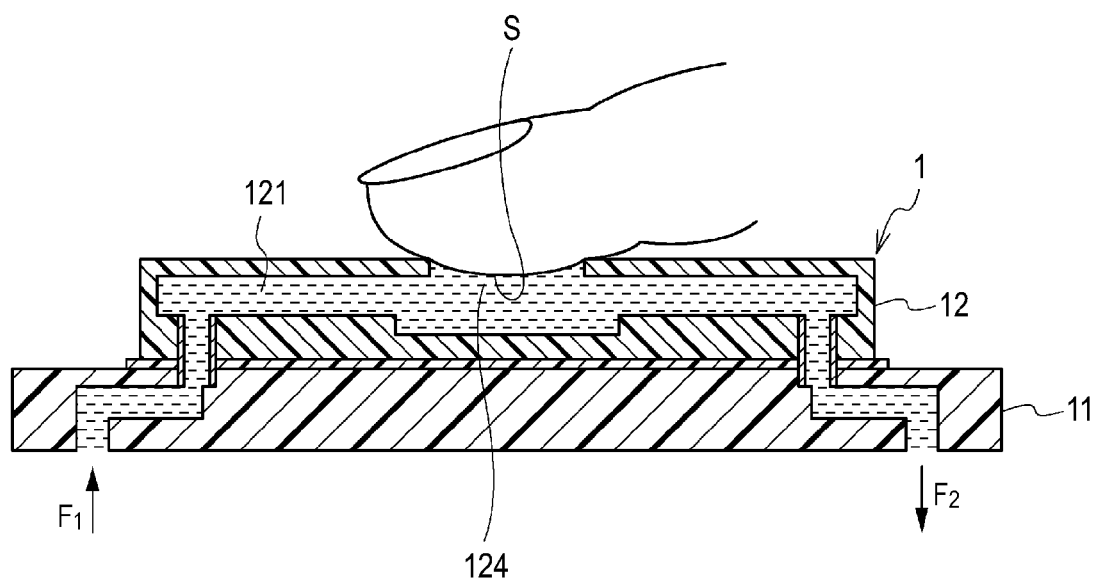
FIG. 5 is a schematic view explaining the procedure of acquiring a physiologically active substance from a body surface.

The configuration of the collecting section 1 is described below with reference to FIGS. 4A and 4B, and FIG. 5. FIGS. 4A and 4B are schematic views explaining the configuration of the collecting section 1, in which FIG. 4A shows a top view, and FIG. 4B shows a cross sectional view taken at P-P in FIG. 4A. FIG. 5 is a cross sectional schematic view explaining the procedure of acquiring the physiologically active substance from the body surface.

The two main components of the collecting section 1 are an anchor substrate 11 and a collection substrate 12. The anchor substrate 11 is provided by being anchored to the main body of the physiologically active substance collecting device A. The collection substrate 12 is detachably provided on the anchor substrate 11, and is replaceable.

The collection substrate 12 includes a channel 121 that flows the solvent sent thereto, an inlet 122 for the solvent flowing into the channel 121, and an outlet 123 for the solvent flowing out of the channel 121. The anchor substrate 11 includes a channel 111 through which the solvent sent from the solvent tank 2 is flown, and a channel 112 through which the solvent sent to the lead-out section 6 is flown. In the figures, arrows $F_1$ and $F_2$ indicate the flow directions of the solvent sent to or drained from the channels in the anchor substrate 11.

The collection substrate 12 has an aperture 124 provided between the inlet 122 and the outlet 123 of the channel 121, and that opens to outside on the upper side of the substrate. The aperture 124 serves to bring the solvent flown in the channel 121 into contact with the body surface. Specifically, as illustrated in FIG. 5, with the body surface S tightly attached to the aperture 124 of the channel 121 flowing the solvent, the solvent filling the channel 121 contacts the body surface S, and the physiologically active substance present on the body surface S is collected in the solvent. The solvent brought into contact with the body surface S is then sent to the lead-out section 6, as indicated by arrow F2.

Here, by selectively introducing the solvent and air from the solvent tank 2 and the air tank 3 into the collecting section 1 using the valves 22 and 32 opened and closed under control as described with reference to FIG. 3, the solvent in contact with the body surface S can be sent to the lead-out section 6 by being separated into predetermined volumes by air. Specifically, with the body surface S tightly attached to the aperture 124, a predetermined volume of solvent is sent to the channel 121. Air is then sent into the channel 121 to separate the flow of the solvent in the channel 121 by air. A predetermined volume of solvent is then resent into the channel 121. By introducing air and the solvent in turn, the solvent that has contacted the body surface S can be sent out to the lead-out section 6 in predetermined volumes separated by air. In this way, the physiologically active substance in the collected sample can be suppressed from being diluted, and samples collected from different living organisms or from different sites of the body surface can be divided and collected in different containers.

The body surface S has been described as being a finger tip. However, the body surface S as the acquisition site of the physiologically active substance is not particularly limited, though skin surface such as finger and palm surface is convenient. The aperture 124 preferably has a shape that allows the skin surface at the acquisition site to be tightly attached, depending on the acquisition site of the physiologically active substance. For more tight attachment to the aperture 124, the body surface S may be fixed to the collection substrate 12 using, for example, an adhesive tape or a band.

As described above, the collection substrate 12 is disposed on the anchor substrate 11, and is replaceable. In this way, different collection substrates 12 with different shapes of apertures 124 can be appropriately replaced and attached according to, for example, the shape and size of the acquisition site of the physiologically active substance. Further, the collection substrate 12 can be replaced to a new one for each sample collection, and cross contamination between the samples can be prevented when collecting samples from different living organisms or from different sites of the body surface, or when collecting samples from the same living organism or body surface at different times. Note that when the collection substrate 12 is not replaced, it is desirable that washing be performed by flowing the solvent or a washing liquid through the collecting section 1 for a predetermined time period, in order to prevent cross contamination between samples.

The channel 111 through which the solvent sent from the solvent tank 2 of the anchor substrate 11 is in communication with the inlet 122 of the collection substrate 12 through a connecting tube 113 (see FIGS. 4A and 4B). The channel 112 through which the solvent sent to the lead-out section 6 of the anchor substrate 11 is in communication with the outlet 123 of the collection substrate 12 through the connecting tube 113. Preferably, the connecting tube 113 is anchored by being press fitted to part of the channel 111 and the channel 112, and be made of hard material (for example, metal). The connecting tubes 113 fitted to the inlet 122 and the outlet 123 become solvent channels upon attaching the collection substrate 12 to the anchor substrate 11, and also serve as members for the registration of the collection substrate 12 on the anchor substrate 11.

It is desirable that a sealing member 13 be inserted between the anchor substrate 11 and the collection substrate 12 to prevent the solvent from leaking out of the surrounding area of the connecting tube 113 at the junction of the collection substrate 12 and the anchor substrate 11 attached in place. Preferably, elastic materials, such as silicon rubber, are used for the sealing member 13. Preferably, the sealing member 13 has a form of a sheet of about the same size as that of the collection substrate 12.

The material of the anchor substrate 11 and the collection substrate 12 may be, for example, glass material such as quartz and borosilicate glass, silicon rubber (such as polydimethylsiloxane; PDMS), acrylic resin (such as polymethylmethacrylate; PMMA), cycloolefin copolymer (COC), or polyetheretherketone (PEEK). The channels and other elements arranged on the substrate may be molded by the wet or dry etching of a glass substrate layer, or may be formed by the nanoimprinting, injection molding, or machining of a plastic substrate layer. It is preferable that the surface of the channels and other elements be subjected to a treatment that makes the adsorption of the physiologically active substance difficult. Such surface treatment may be performed using, for example, 2-methacryloyoxyethyl phosphorylcholine (MPC), and polyethylene glycol (PEG). Preferably, the collection substrate 12 is disposable.

Figure 6A:
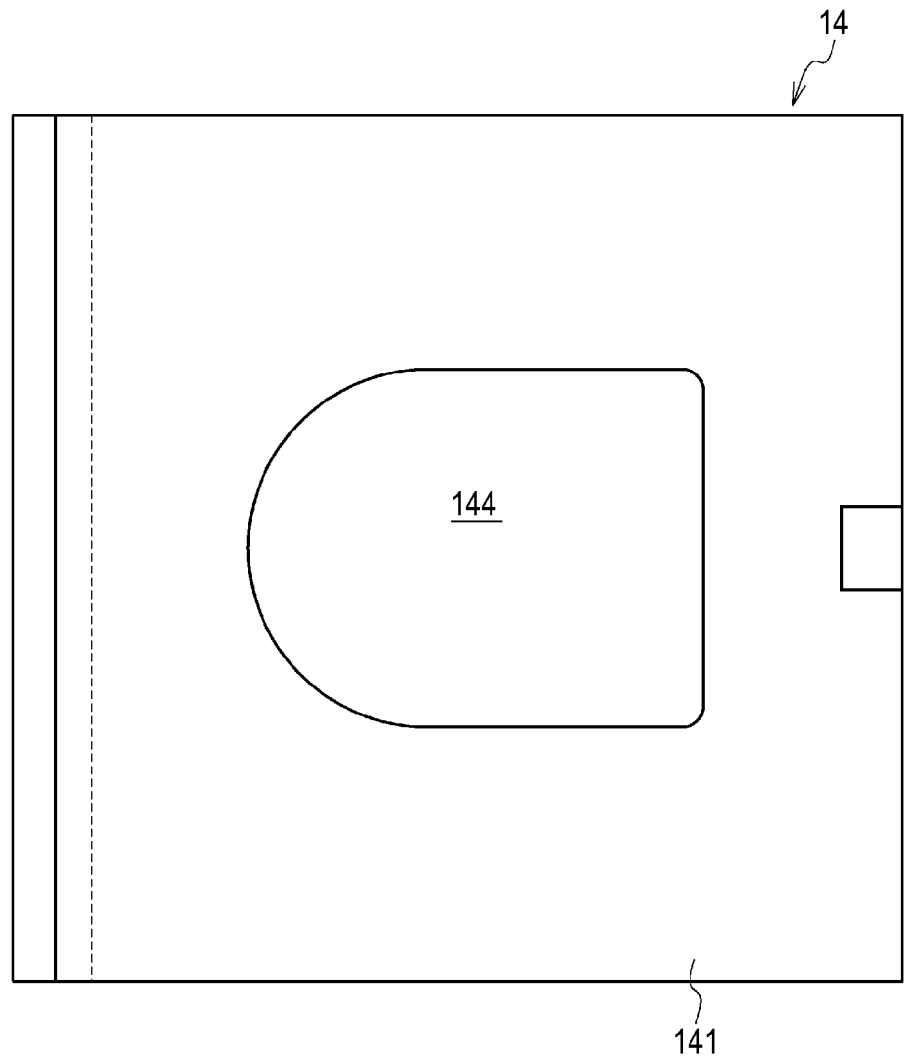
FIGS. 6A and 6B are schematic views explaining the configuration of a holder.
Figure 6B:
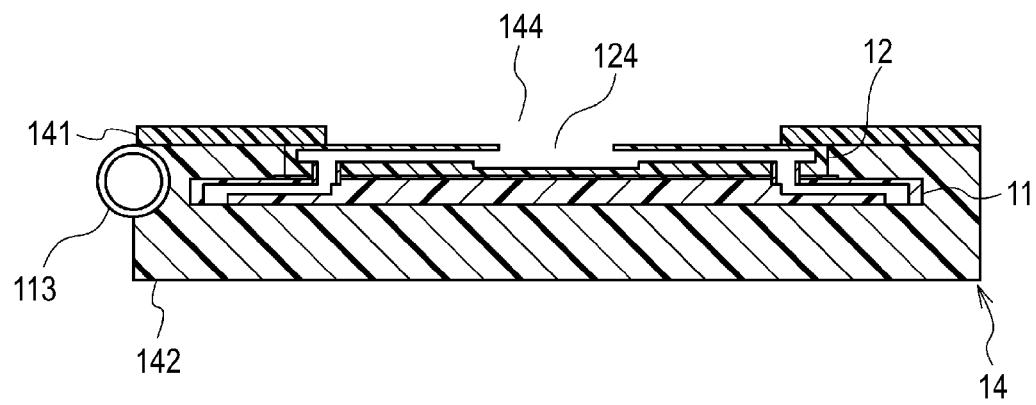
Figure 6C:
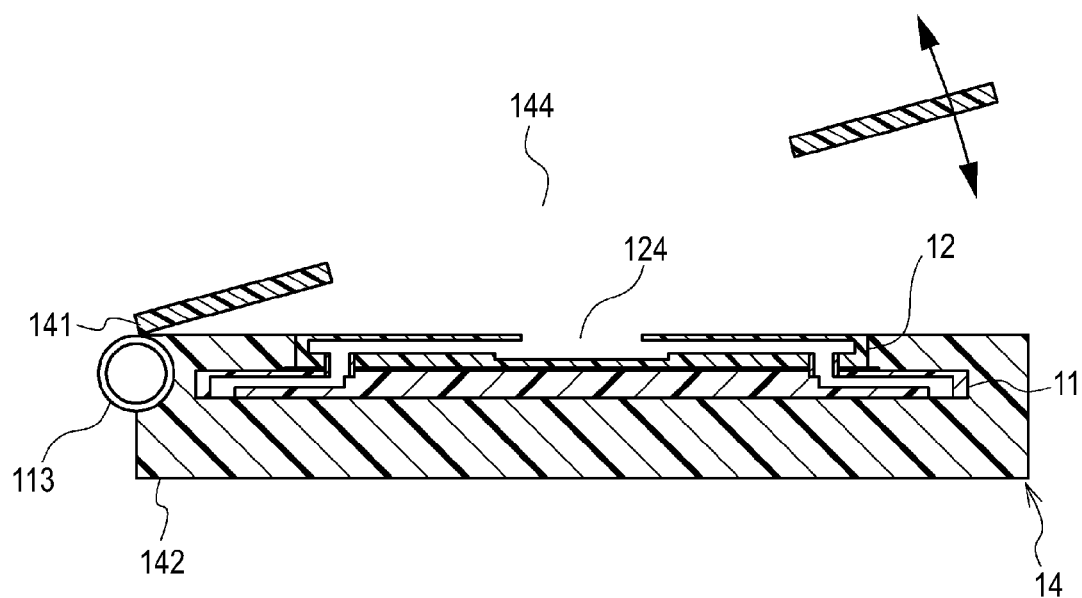
FIG. 6C is a schematic view explaining the operation of the holder.

FIGS. 6A to 6C are schematic views explaining the configuration and operation of a holder used to hold the collection substrate 12 attached to the anchor substrate 11. FIG. 6A represents a top view, and FIGS. 6B and 6C represent cross sectional views.

As illustrated in the figures, a holder 14 includes an upper plate 141, a lower plate 142, and a hinge 143 that joins these plates. The upper plate 141 has a window 144 in a portion corresponding to the aperture 124 of the collection substrate 12 held by the holder 14. For the replacement of the collection substrate 12, the upper plate 141 is configured to open and close in the direction of arrow, using the hinge 143 as a fulcrum (see FIG. 6C).

The anchor substrate 11 is anchored to the main body of the device with the lower plate 142 of the holder 14. With the anchor substrate 11 and the collection substrate 12 sandwiched between the upper plate 141 and the lower plate 142 of the holder 14, the upper plate 141 presses down the collection substrate 12 attached to the anchor substrate 11. In this way, the holder 14 tightly holds the anchor substrate 11 and the collection substrate 12 via the sealing member 13 placed between the two substrates (see FIG. 5), and thus prevents the solvent from leaking out of the surrounding area of the connecting tube 113.

(4) Supplying Unit

Figure 7:
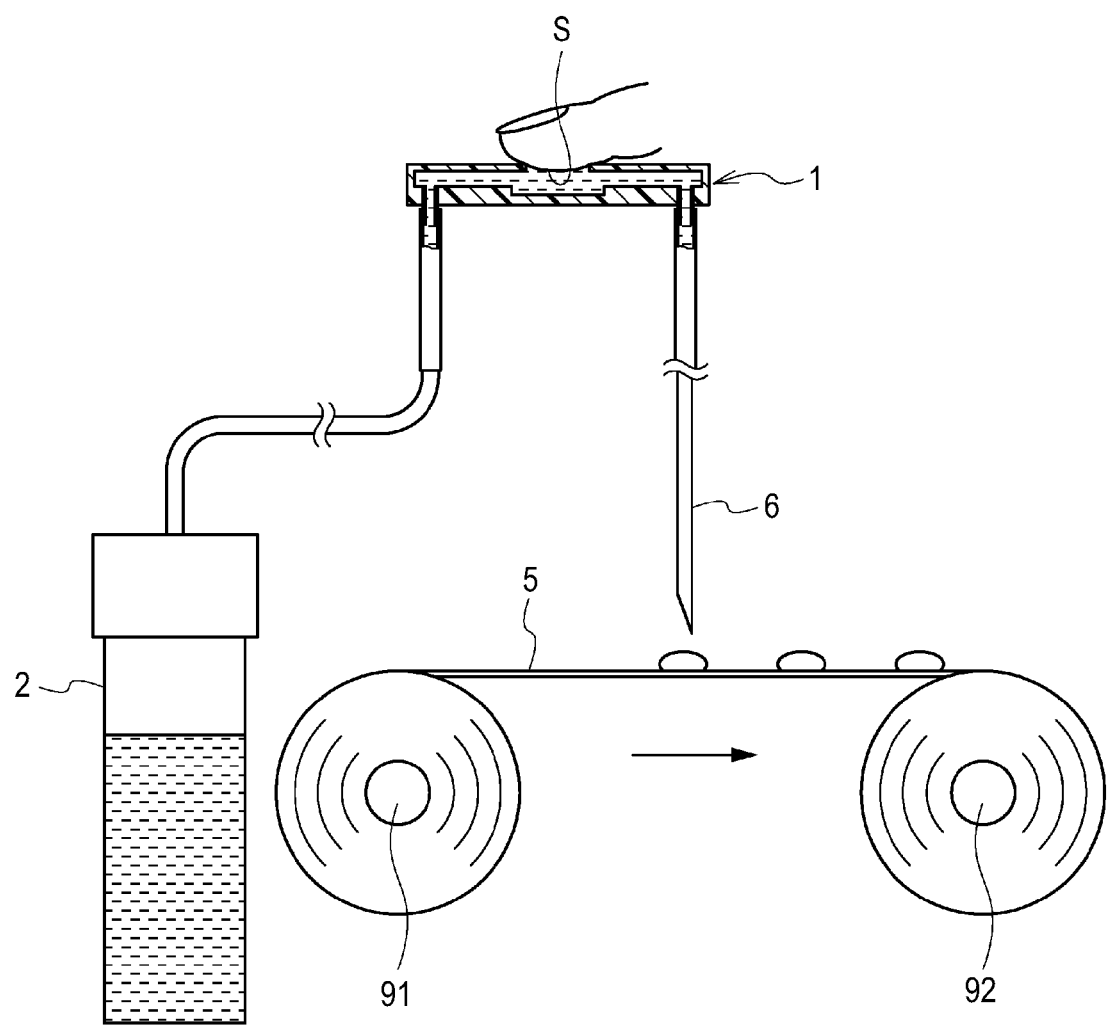
FIG. 7 is a schematic view explaining the operation of a supplying unit.

The operation of the supplying unit is described below with reference to FIG. 7.

In the biological substance collecting device A, the absorber 5 that absorbs and holds the solvent drained from the lead-out section 6 is sent to underneath the lead-out section 6 by the supplying unit that includes a first core 91. The absorber 5 is stored by being wound around the first core 91, and reeled out to underneath the lead-out section 6 by the rotation of the first core 91. The absorber 5 is sent in the direction of the arrow in the figure.

The solvent sent from the solvent tank 2 to the collecting section 1 and contacted the body surface S is dropped from the lead-out section 6 either intermittently or continuously. The absorber 5 sent to underneath the lead-out section 6 accepts and absorbs the solvent. The absorber 5 holding the solvent is sent to a second core 92, and stored by being wound around the second core 92. Note that, the draining of the solvent through the hole at the end of the lead-out section 6 is controlled at appropriate timing with the valve 62 and the system control unit described in FIG. 3.

Because the sample is absorbed and held on the absorber 5 stored by being wound around the second core 92, the biological substance in the sample can be preserved more stably than in the method in which the sample is collected and preserved in the form of a solution in a container such as a tube. Further, the device configuration can be simplified for the miniaturization of the device.

Further, by drying and evaporating the solvent for removal from the absorber 5 absorbing and holding the sample, the biological substance can be preserved even more stably, and can be prevented from degradation more effectively than in the method in which the sample is preserved in the form of a solution. The solvent may be evaporated by natural drying, more preferably with the use of drying unit such as a blower and a heater.

Figure 8A:
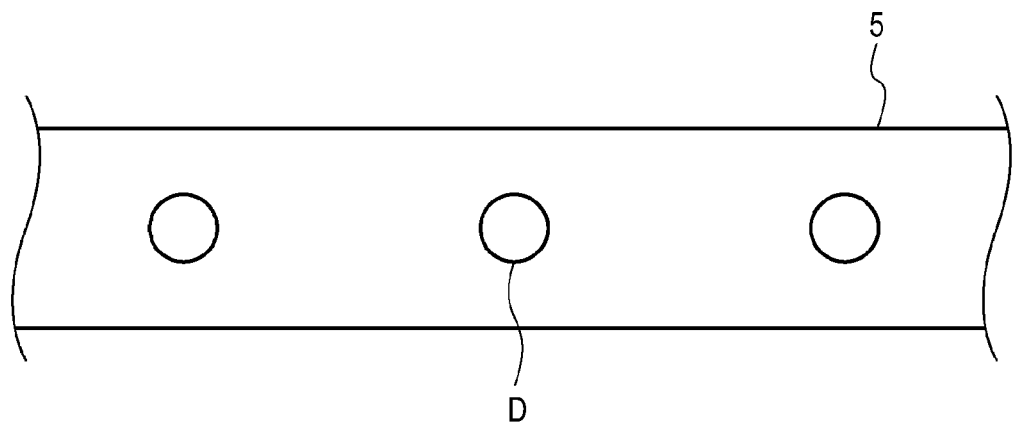
FIGS. 8A and 8B are schematic views explaining the shape of an absorber.

Preferably, the absorber 5 is shaped in the form of a belt (tape) in order to be wound around the first core 91 or the second core 92. FIG. 8A schematically represents the absorber 5 having a tape shape, and solvent D dropped from the lead-out section 6. In order to prevent the solvent D from seeping to the other side of the absorber 5 after being dropped, the other side of the absorber 5 is preferably coated with material that does not pass the solvent.

Diffusive mixing of solvent D needs to be prevented when collecting samples from different living organisms or from different sites of the body surface, or when collecting samples from the same living organism or body surface at different time points or with the passage of time. It is therefore preferable that the absorber 5 having a tape shape be impregnated with impermeable material to the solvent at predetermined intervals, and the solvent D be dropped onto each part divided by the material.

Figure 8B:
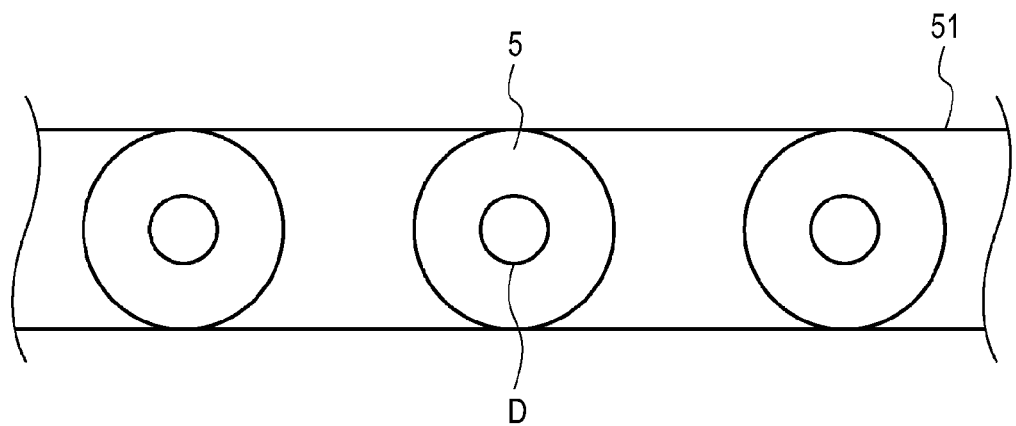

Diffusive mixing of solvent D also can be prevented by the configuration in which, as illustrated in FIG. 8B, absorbers 5 of a predetermined shape (circular in the figure) are disposed on a tape-shaped base 51 made of material impermeable to the solvent. In this case, the absorbers 5 may be detachably disposed on the base 51. The material of the base 51 may be appropriately selected according to the type of the solvent used. For example, a general-purpose plastic film can be used as the base 51.

The absorber 5 was described as being preserved by being wound around the second core 92 after absorbing the solvent. This is preferable in collecting large amounts of sample, because the storage efficiency of the absorber 5 in the device can be improved by winding the absorber 5. It should be noted, however, that the second core 92 is not necessarily required in the physiologically active substance collecting device A. Specifically, the absorber having absorbed the solvent may be successively sent out of the device through an outlet provided in the main body of the device, without being wound.

Further, when the absorber 5 is detachably disposed on the base 51 as in FIG. 8B, the absorber 5 may be detached from the base 51 and preserved by being stacked in the device, using a mechanism provided to detach the absorber 5 from the base 51 after the absorber 5 has absorbed the solvent.

Further, in the physiologically active substance collecting device A, the supplying unit that sends the absorber 5 to the lead-out section 6 is not limited to the foregoing configuration that includes the first core 91. Specifically, the supplying unit may be configured to send the absorber 5, prepared as cards of a predetermined shape, to the lead-out section 6 one by one, and to send the absorber 5 from the lead-out section 6 after the absorber 5 has absorbed the solvent.

The physiologically active substance collecting device A described above can be used to acquire a physiologically active substance from the body surface such as finger and palm surface, and can thus collect physiologically active substances in a simpler, more minimally invasive fashion than in methods that collect physiologically active substances from blood, urine, or saliva. Further, because the physiologically active substance acquired is that that is present on the body surface, the physiologically active substance can be acquired without making the subject strongly aware of the collection procedure, unlike the collection from bodily fluids such as blood, urine, and saliva.

Further, in the physiologically active substance collecting device A, because the physiologically active substance secreted or permeated to the body surface is collected, the physiologically active substance can be collected over a time course or on a steady basis. Further, because the physiologically active substance secreted or permeated to the body surface is collected, the physiologically active substance can be collected while the physiologically active substance is being metabolized in the body.

2. Physiologically Active Substance Collecting Device According to Variations of First Embodiment The physiologically active substance collecting device A according to First Embodiment has been described through the collecting section 1 formed by attaching the collection substrate 12 with the holder 14 to the anchor substrate 11 anchored on the device main body. However, the configuration of the collecting section 1 may be varied as follows.

(1) First Variation

Figure 9:
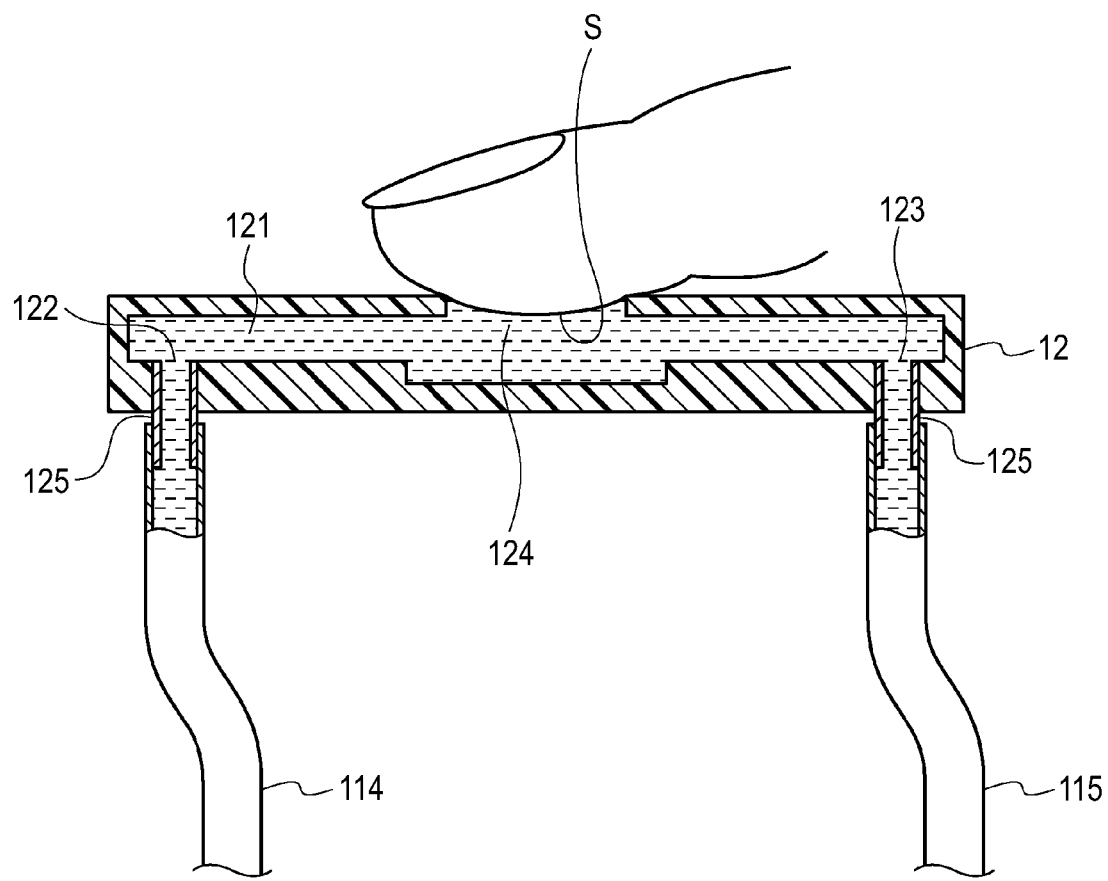
FIG. 9 is a schematic view explaining the configuration of a variation of the collecting section.

FIG. 9 is a schematic view explaining the configuration of a variation of the collecting section provided in the physiologically active substance collecting device according to the embodiment of the present disclosure. The figure represents the procedure of acquiring a physiologically active substance from the body surface at the collecting section. The collecting section according to the present variation is configured to enable the collection of a physiologically active substance from the body surface S with the collection substrate 12 separated from the anchor substrate 11 and from the main body of the device.

The collection substrate 12 is connected to the anchor substrate 11 (not illustrated) via tubes 114 and 115. The solvent (and air) sent from the anchor substrate 11 side is introduced to the channel 121 through the tube 114. After contacting the body surface S at the aperture 124, the solvent is sent to the anchor substrate 11 side through the tube 115. In FIG. 9, slots 125 are fitted to the inlet 122 and the outlet 123 of the channel 121, and connected to the tubes 114 and 115. The slots 125 may be metal or plastic tubes.

The collecting section according to the present variation is configured to include the collection substrate 12 separately provided from the device main body. Thus, by appropriately setting the length of the tubes 114 and 115, for example, the procedure of pressing a finger tip against the collection substrate 12 can be made with the collection substrate 12 brought close to the hand. Alternatively, the collection substrate 12 may be attached to the skin surface of the trunk to collect a physiologically active substance. When collecting a physiologically active substance from the skin surface of the trunk, the collection substrate 12 may be attached to the skin using an adhesive tape, or by wrapping a band around the trunk.

(2) Second Variation

Figure 10A:
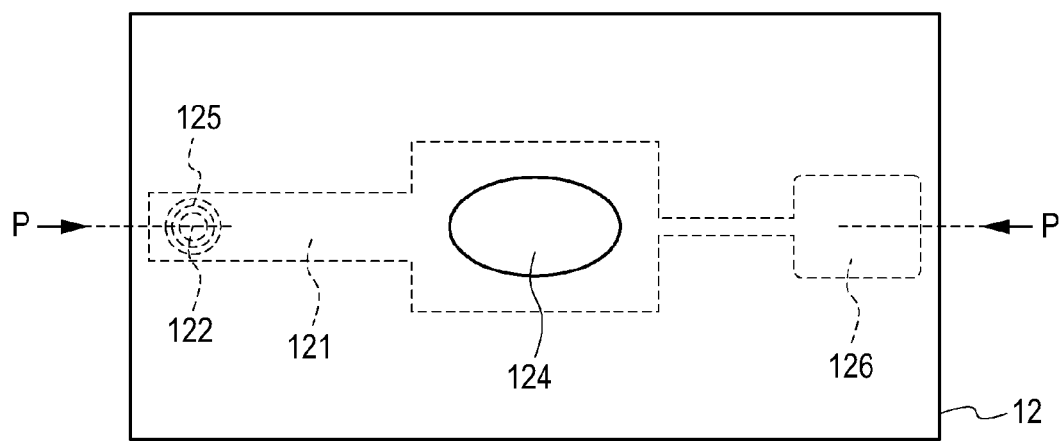
FIGS. 10A and 10B are schematic views explaining the configuration of yet another variation of the collecting section.
Figure 10B:
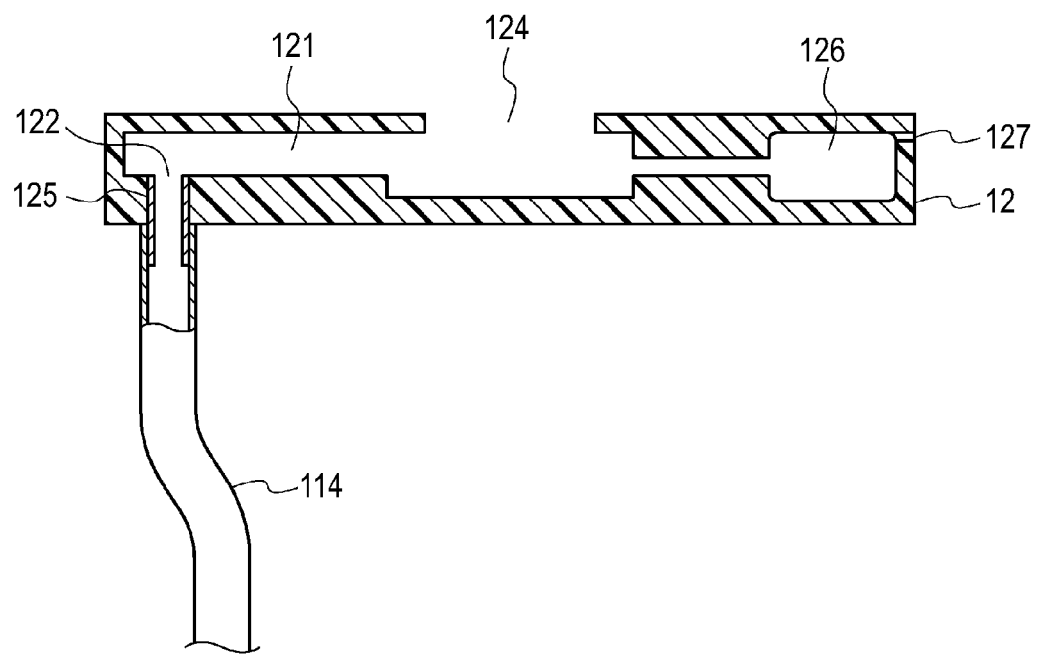

FIGS. 10A and 10B are schematic views explaining the configuration of another variation of the collecting section provided in the physiologically active substance collecting device according to the embodiment of the present disclosure. FIG. 10A represents a top view, and FIG. 10B a cross sectional view taken at P-P in FIG. 10A. The collecting section according to the present variation includes a collection region 126 formed in the collection substrate 12, and that stores the solvent that has contacted the body surface at the aperture 124.

The slot 125 is provided at the inlet 122 of the collection substrate 12, and is connected to the tube 114 through which the solvent sent from the anchor substrate 11 is introduced to the channel 121. The solvent introduced to the channel 121 and contacted the body surface at the aperture 124 is introduced to the collection region 126 and stored therein. In the figures, an air vent 127 is provided through which the air inside the collection region 126 is evacuated by being pushed by the introduced solvent.

The collecting section according to the present variation is configured to store a sample in the collection region 126 internally provided for the collection substrate 12, and is therefore suited for a single or a few collections of samples. Cross contamination between samples can be avoided by replacing the collection substrate 12 for each sample collection. Further, samples can be collected more easily, because the use of a collecting unit including the lead-out section 6 is not necessary.

The collection region 126 and the air vent 127 can be molded in the collection substrate 12 by the wet or dry etching of a glass substrate layer, or by the nanoimprinting, injection molding, or machining of a plastic substrate layer. More than one collection region 126 may be provided. In this case, the channel 121 downstream of the aperture 124 is branched and connected to each collection region 126. The branching portion of the channel 121 into the collection regions 126 may be provided with a switch valve that sends the solvent to one of the collection regions 126.

(3) Third Variation

Figure 11A:
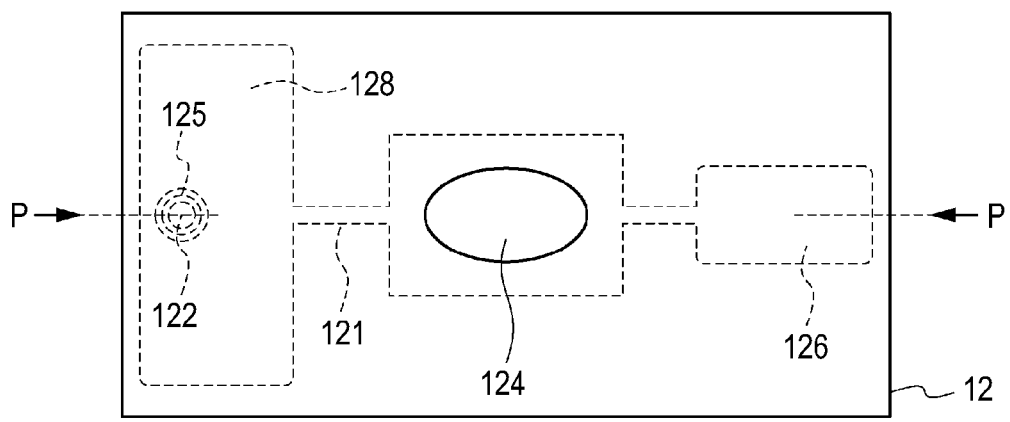
FIGS. 11A and 11B are schematic views explaining the configuration of still another variation of the collecting section.
Figure 11B:
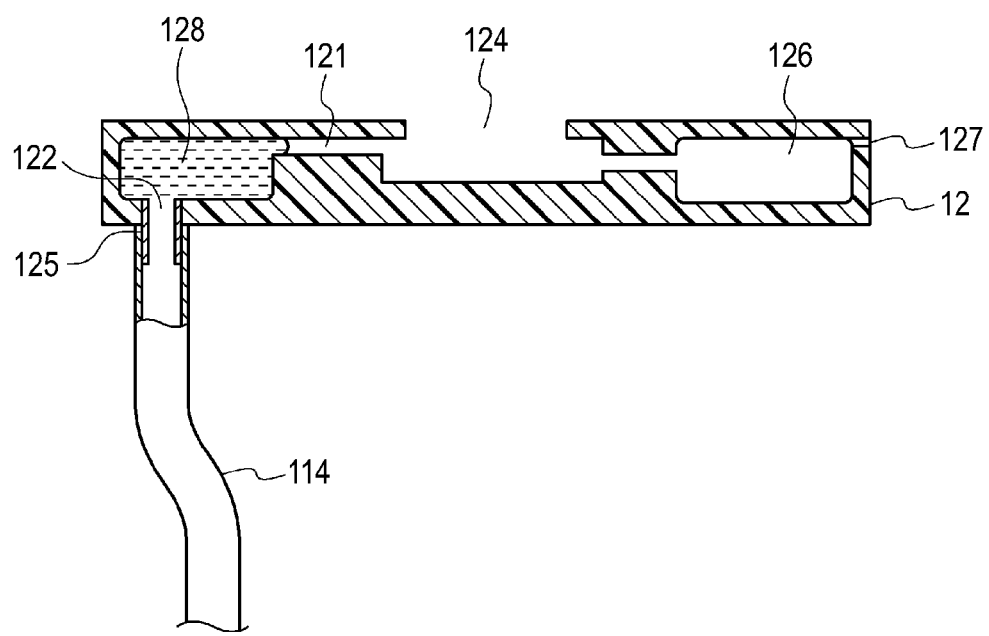

FIGS. 11A and 11B are schematic views explaining the configuration of yet another variation of the collecting section provided in the physiologically active substance collecting device according to the embodiment of the present disclosure. FIG. 11A represents a top view, and FIG. 11B a cross sectional view taken at P-P in FIG. 11A. The collecting section according to the present variation includes a solvent storage region 128 formed in the collection substrate 12, and that can store the solvent for later use.

The solvent required for a single or a few sample collections can be injected to the solvent storage region 128 and stored therein in advance. The slot 125 is provided at the inlet 122 of the collection substrate 12, and is connected to the tube 114 through which the air sent from the anchor substrate 11 is introduced to the channel 121. The air introduced to the channel 121 pushes the solvent stored beforehand in the solvent storage region 128. The solvent then contacts the body surface at the aperture 124, and is introduced to the collection region 126 and stored therein.

The collecting section according to the present variation enables sample collection with the use of a solvent stored beforehand in the solvent storage region 128 internally provided for the collection substrate 12, and is therefore preferred for sample collections in which the solvent is changed for each sample.

The solvent storage region 128 can be molded in the collection substrate 12 by the wet or dry etching of a glass substrate layer, or by the nanoimprinting, injection molding, or machining of a plastic substrate layer.

3. Biological Information Acquisition Method

The biological information acquisition method using the physiologically active substance collecting device according to the embodiment of the present disclosure is described below.

As described above, the physiologically active substance collecting device according to the embodiment of the present disclosure acquires the physiologically active substance present on the body surface, and can thus acquire physiologically active substances without making a subject strongly aware of the collection procedure, unlike collection from bodily fluids such as blood, urine, and saliva. Further, because the physiologically active substance secreted or permeated to the body surface is collected, the physiologically active substance can be collected over a time course or on a steady basis. Further, because the physiologically active substance secreted or permeated to the body surface is collected, the physiologically active substance can be collected while the physiologically active substance is being metabolized in the body.

The physiologically active substance collecting device according to the embodiment of the present disclosure can thus be used to collect the physiologically active substance and acquire the collected physiologically active substance from the subject over a time course or on a steady basis, and thus enables real-time sensing of the biological information from the quantified value, without causing stress or emotional changes in the subject.

(1) Extraction of Physiologically Active Substance

In the physiologically active substance collecting device according to the embodiment of the present disclosure, the physiologically active substance acquired from the body surface at the collecting section is preserved by being held on the absorber. The physiologically active substance can be extracted from the absorber by dipping the absorber in an extraction solvent. Alternatively, an extraction solvent may be dropped onto the absorber, and the physiologically active substance may be extracted by centrifugation after the solvent is thoroughly absorbed.

When the absorber has a tape shape (see FIG. 8A), the absorber is cut as required, and placed in a tube or the like filled with a solvent. When the absorber is formed into a predetermined shape and disposed on a tape-shaped base (see FIG. 8B), the absorber is used after being cut out from the base. When the absorber is detachable from the base, the absorber may be detached and directly placed in a tube or the like filled with a solvent.

The solvent used for the extraction of the physiologically active substance may be the same solvent used for the collection, or a different solvent may be used. For example, it is considered possible to use a collection solvent that is not harmful to the body surface upon contact, and use an extraction solvent that easily dissolves the physiologically active substance.

(2) Quantification of Physiologically Active Substance

The quantification of the physiologically active substance redissolved in the solvent may be performed using, for example, liquid chromatography (HPLC), a surface plasmon sensor (SPR), or a quarts crystal microbalance sensor (QCM). Known techniques such as enzyme immunoassay and radioimmunoassay also may be used for the quantification.

HPLC, SPR, and QCM do not require the labeling required in enzyme immunoassay and radioimmunoassay, and thus simplify the quantification procedure. Use of SPR or QCM is more desirable in terms of measurement accuracy. In HPLC, physiologically active substances are detected as peaks on a chromatograph, and thus inclusion of foreign substance signals or noise in the peak intensity may lower measurement accuracy. On the other hand, SPR and QCM detect physiologically active substances using antibodies immobilized on the sensor surface, and thus can have high measurement accuracy based on antibody specificity. Another advantage of SPR and QCM over HPLC is higher throughputs.

(3) Acquisition of Biological Information

The biological information is acquired using the quantified value of the physiologically active substance as an index. Specifically, for example, the amounts of physiologically active substances in large numbers of healthy subjects over a predetermined time period in a day are measured, and a standard change curve that defines a standard range of concentration changes of physiologically active substance amounts is calculated based on the measurement result. The amount of physiologically active substance in a subject is then compared with the standard change curve to determine biological information.

Examples of the biological information acquired using the physiologically active substance collecting device according to the embodiment of the present disclosure include information concerning stress, emotion, menstrual cycle, and exercise effects. Other examples include sleepiness (wakefulness level), health conditions, and circadian rhythm (biological rhythm).

Concerning stress, there is a well known correlation between the stress load on a living organism and the secretion levels of cortisol, corticosterone, and cortisone (hereinafter, collectively referred to as "cortisols"), as described in Patent Documents 3 and 4. As used herein, "secretion levels" are the secretion levels in blood; specifically, the term has the same meaning as "blood concentration".

Concerning emotion such as excitement, fear, anger, aggression, comfort, anxiety, and sorrow, there is a known correlation with the secretion levels of norepinephrine, epinephrine, dopamine, and L-DOPA, a precursor substance of these (hereinafter, collectively referred to as "catecholamines"). The correlation between emotion and the secretion levels of serotonin, a member of monoamines as are catecholamines, has also been elucidated.

For example, there is a report that the noradrenaline levels in saliva are different before and after a psychosocial test performed to give anxiety or fear to a subject (see Study of salivary catecholamines using fully automated column-switching high-performance liquid chromatography, Journal of Chromatography. B, Biomedical Sciences and Applications, 1997 Jul. 4; 694 (2): 305-16).

Further, as is well known, estrone (E1), estradiol (E2), and estriol (E3) (hereinafter, collectively referred to as "estrogens") control the menstrual cycle of a living organism, and their secretion levels vary in correlation with the menstrual cycle.

It is also known that effective exercises promote secretion of growth hormone. The secretion of growth hormone promotes muscle and bone growth, and facilitates the recruitment of body fat to increase fat combustion efficiency. It is therefore believed that the effects of exercises such as in muscle enhancement and dieting have a correlation with the secretion levels of growth hormone.

Thus, for example, the quantified value of cortisols can be used to obtain information concerning the stress placed on a living organism. Specifically, for example, the secretion levels of cortisols in large numbers of healthy subjects are measured, and a standard change curve that defines a standard range of concentration changes of cortisols is calculated based on the measurement result. The secretion levels of cortisols in a subject are then measured, and the result is compared with the standard change curve. For example, if the measured secretion levels deviate from the standard change curve, it can be determined that the subject is under chronic stress.

Further, for example, the secretion levels of cortisols in a subject under normal conditions are measured, and a standard change curve is calculated from the measurement results. The standard change curve can then be compared with the secretion levels of cortisols in the subject at a given time to determine whether the subject at the given point of time is under stress or relaxing.

Aside from the cortisols, monoamines, estrogens and growth hormones, the combinations of index physiologically active substances and biological information presented in Table 1 are known. In the embodiment of the present disclosure, by using these combinations, information concerning biological information can be obtained based on the positive or negative correlation between the quantified value of the physiologically active substance and biological information.

TABLE 1

| Biological information | Physiologically active substance | |
|---|---|---|
| Stress | Steroid hormones | Cortisol, corticosterone, cortisone |
| | Peptides | Neuropeptide Y (NPY) |
| Emotion (aggression) | Steroid hormones | Testosterone, dihydrotestosterone (DHT), dehydroepiandrosterone (DHEA), dehydroepiandrosterone sulfate (DHEAS) |
| Emotion (excitement, fear, anger, etc.) | Monoamines (catecholamines) | Noradrenaline (norepinephrine), adrenaline (epinephrine), L-DOPA |
| Emotion (comfort) | Monoamines (catecholamines) | Dopamine |
| | Peptides | Endorphin |
| Emotion (anxiety) | Monoamines | Serotonin |
| | Peptides | Oxytocin, vasopressin, galanin |
| Sleepiness (wakefulness level) | | Melatonin |
| Menstrual cycle | Steroid hormones | Estrone (E1), estradiol (E2), estriol (E3) |

Note that the physiologically active substances presented in Table 1 are merely examples, and other catecholamines, for example, such as metanephrine, normetanephrine, 3-methoxy-4-hydroxymandelic acid, 3-methoxy-4-hydroxyphenylglycol, 3,4-dihydroxymandelic acid, 3,4-dihydroxyphenylglycol, 3,4-dihydroxyphenylacetic acid, 3-methoxytyramin, homovanillic acid, 5-hydroxyindoleacetic acid, and vanillylmandelic acid also can be used as the index of biological information. Other examples of steroid hormones that also can be used as the index of biological information include aldosterone, deoxycortisterone, androstenedione, progesterone, 11-deoxycorticosterone, pregnenolone, 11-deoxycortisol, 17-hydroxyprogesterone, 17-hydroxypregnenolone, and cholecalciferol (vitamin D).

Other examples of physiologically active substances that also can be used as the index of biological information include: hypophysiotropic hormones such as corticotropin release hormone (CRH), growth hormone release hormone (GRH), somatostatin (growth hormone secretion inhibiting hormone), gonadotropin release hormone (GnRH), prolactin release hormone (PRH), prolactin inhibiting hormone (PIH), thyrotropin release hormone (TRH), and thyroid-stimulating hormone (TSH); thyroid hormones such as thyroxine and triiodothyronine; and various other hormones and neurotransmitters, including chromogranin A, adrenocorticotropic hormone (ACTH), luteinizing hormone (LH), insulin-like growth factor I (IGF-I), prolactin, proopiomelanocortin (POMC), oxytocin, α-melanocyte stimulating hormone (α-MSH), glucagon, ghrelin, galanin, motilin, leptin, gastrin, cholecystokinin, selectin, activin, inhibin, neurotensin, bombesin, substance P, angiotensin I, II, enkephalin, orexin A, B, anandamide, acetylcholine, histamine, glutamic acid, glycine, aspartic acid, pyrimidine, adenosine, adenosine triphosphate (ATP), GABA, FMRF amide, peptide YY, Agouti-related peptide (AGRP), cocaine- and amphetamine-regulated transcript (CART), calcitonin gene-related peptide (CGRP), glucagon-like peptide 1, 2 (GLP-1, 2), vasoactive intestinal peptide (VIP), gastrin release peptide (GRP), and melanin-concentrating hormone (MCH).

The correspondence between the physiologically active substances and biological information is not limited to the foregoing examples. For example, serotonin also can be used as an index of schizophrenia or insomnia as for emotions, and estrogens also can be used as an index of infertility, symptoms of menopause, or a manic-depressive state as for the menstrual cycle. In fact, the combination of the physiologically active substance and the corresponding biological information may be any combination elucidated to date.

The biological information acquisition method according to the embodiment of the present disclosure can be used for the diagnosis, prevention, or prognostic study of various diseases based on the health conditions of a living organism found by using, for example, the physiologically active substances presented in Table 1 as an index. Specifically, for example, a diagnosis can be made to find the presence or absence of chronic stress through the measurement of cortisols, and the diagnosis result can be used for the prevention or prognostic study of chronic stress. It is also considered possible to make, for example, a diagnosis for the presence or absence of a carcinoid tumor through the measurement of catecholamines, or a diagnosis for schizophrenia, insomnia, endogenous depression, dumping syndrome, or migraine through the measurement of serotonin. Further, estrogens can be measured for easy diagnosis of menstrual cycle, and for the diagnosis of estrogen-dependent diseases (such as infertility, breast cancer, uterine fibroid, and endometriosis), and symptoms of menopause.

The secretion levels of growth hormone is known to decrease with age. Involvement of growth hormone in the onset of lifestyle-related disease such as diabetes, high-blood pressure, and hyperlipidemia through its action on the metabolism of carbohydrates, proteins, and lipids is also known. Other examples of growth hormone-related disease include growth hormone deficiency, hypopituitarism, hypothyroidism, and obesity, which involve decreased secretion levels of growth hormone. Other examples include gigantism, acromegaly, ectopic hormone-producing tumor, severe undernutrition (such as anorexia nervosa), and chronic kidney failure, which involve increased secretion levels of growth hormone. Thus, the growth hormone measurement by the physiologically active substance measurement method according to the embodiment of the present disclosure allows the extent of aging to be determined, and enables the diagnosis of various diseases, including lifestyle-related disease and growth hormone-related disease.

EXAMPLES

Example 1

Quantification of Cortisols

1. Acquisition of Cortisol from Skin Surface

Cortisol was acquired from the skin surface of the fingers of six subjects, three times a day (10, 14, 18 o'clock) for 4 days, using the two methods below.

(1) Collection Using Microtube

Figure 12A:
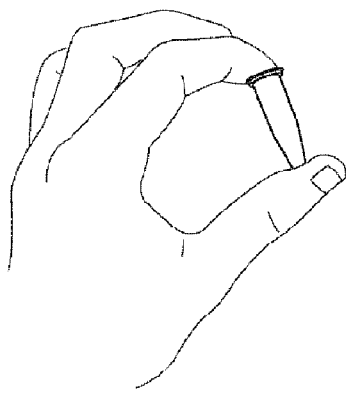
FIGS. 12A and 12B are schematic views explaining methods of acquiring a physiologically active substance from the skin surface of a finger (Example 1).

The finger tip of index finger was gently wiped with a paper towel soaked with ethanol. The lower end of a microtube containing 1% ethanol water (50 μL) was held with the thumb, with the upper opening touching the finger tip of the index finger (see FIG. 12A). The microtube was inverted between the index finger and thumb to contact the 1% ethanol water to the skin surface of the index finger for 1 min. Here, the finger tip was wiped in advance with a paper towel to remove foreign substances present on the skin surface, and to remove the possible accumulation of cortisol on the skin surface.

(2) Collection Using Syringe

Figure 12B:
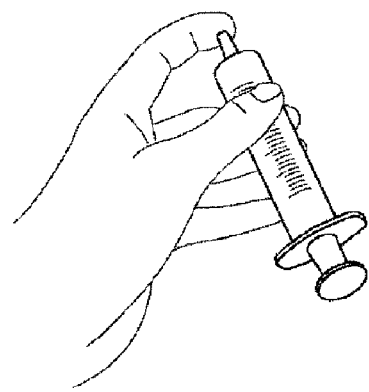

The finger tip of index finger was gently wiped with a paper towel soaked with ethanol. After charging 1% ethanol water (50 μL) into the tip of a syringe, the syringe was held with the thumb and middle finger, with the tip of the index finger touching the syringe (see FIG. 12B). The piston of the syringe was then pulled with the right hand to create a negative pressure therein and suck the skin surface, and to thereby contact the 1% ethanol water to the skin surface of the index finger for 1 min. This method is more advantageous than the collection using a microtube described in (1) above, because the method enables the 1% ethanol water contacted to the skin surface to be collected in higher yield based on the negative pressure in the syringe.

2. Quantification Using High-Performance Liquid Chromatography (HPLC)

40 μL of 1% ethanol water contacted to skin surface (hereinafter, simply "sample") was collected in a vial. 30 μL of the sample was then analyzed by high-performance liquid chromatography (NANOSPACE SI-2, SHISEIDO).

2.5% acetonitrile water was flown at a flow rate of 100 μL/min, using CAPCELLPAK MF Ph-1 (column size 1.5 mm ID×35 mm, column temperature 35° C., SHISEIDO) as a pretreatment column. 10 mM phosphate buffer (pH 6.8)/CH3CN=78/22 was flown at a flow rate of 100 μL/min using CAPCELLPAK C18 UG120 (column size 1.5 mm ID×250 mm, column temperature 35° C., SHISEIDO) as an analytical column. An ultraviolet absorbance detector (wavelength 242 nm UV) was used for the detection, and the measurement was made for 50 min.

Standard cortisol (Wako Pure Chemical Industries, Ltd.) was prepared as a 0.5 μM cortisol/cortisone aqueous solution, and a preliminary study was made. In the preliminary study, the valve switching time from the pretreatment column to the analytical column (2.7 to 4.4 min from the start of measurement), and the cortisol efflux time (36 to 38 min from the same reference point) were confirmed.

Figure 13:
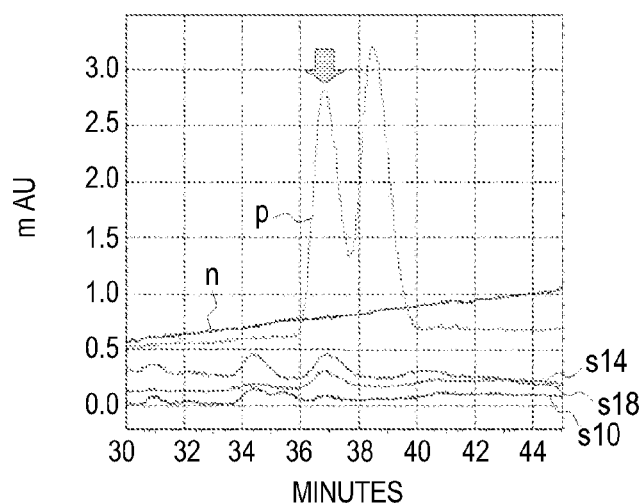
FIG. 13 is a diagram representing the results of the measurement of cortisol level in one subject using high-performance liquid chromatography (HPLC) (Example 1).

FIG. 13 represents the measurement results of the cortisol levels in samples collected from one subject three times a day (10, 14, 18 o'clock). In the figure, cortisol peaks can be confirmed in the samples collected at each time (s10, s14, s18). As indicated by block arrow, the peaks correspond to the standard peak p. Note that, the measurement result for 1% ethanol water that was not contacted to the skin is indicated by n.

Figure 14:
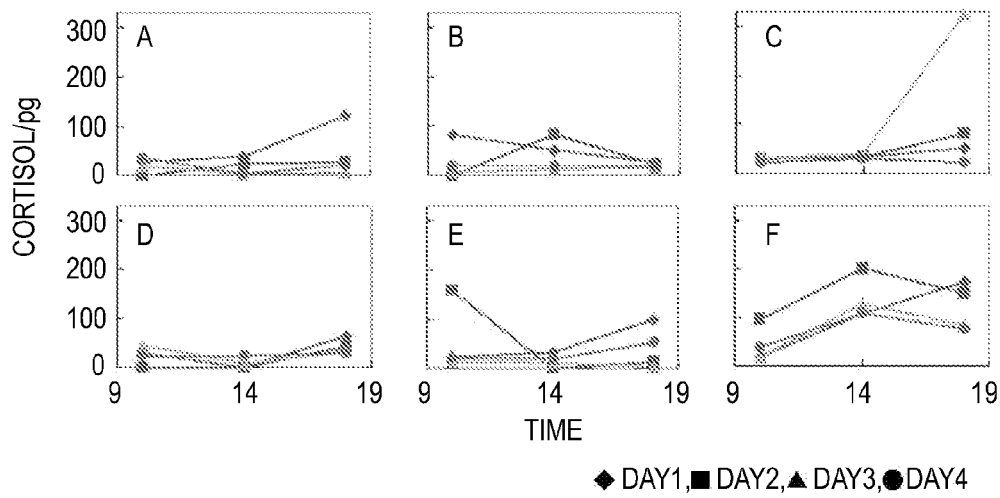
FIG. 14 in A to F represents the results of the measurement of cortisol level in six subjects using high-performance liquid chromatography (HPLC) (Example 1).

FIG. 14 in A to F represents the cortisol levels (pg) calculated from the peak area determined based on the baseline, using the standard curve. The results represented in FIG. 14 are the results of the measurements performed for six subjects (subjects A to F) for 4 days. The results confirmed that cortisol could be collected from the skin surface in amounts ranging from several picograms to as high as 300 picograms, though the results varied from one individual to another, and depending on the measurement time.

3. Quantification Using Surface Plasmon Sensor (SPR)

The samples prepared using the method of Example 1 (collection by syringe) were analyzed by indirect competitive SPR using a surface plasmon sensor (Biacore X, Biacore). The analysis was performed according to the following procedure.

(1) Immobilization of Cortisol on SPR Sensor Surface

An SA chip (Biacore) including streptavidin pre-immobilized on surface was used as the SPR sensor. Standard cortisol was biotinylated, and, after being dissolved in Acetate 4.0 (Biacore), injected at a flow rate of 10 µL/min (100 µL) to immobilize the cortisol on the SPR sensor surface through avidin-biotin reaction. The immobilized cortisol was about 150 RU.

(2) Creation of Standard Curve

First, standard cortisol as a 10 mM DMSO (dimethyl sulfoxide) solution was serially diluted using 1% ethanol water to prepare 100, 50, 25, 12.5, 6.25, 3.13, 1.56, and 0.78 nM standard solutions. 40 µL of the standard solution of each concentration was thoroughly mixed with 40 µL of a 5 ng/mL anti-cortisol antibody solution to run a binding reaction. After the binding reaction, 25 µL of the standard sample solution was injected at 10 µL/min, at 25° C. Note that mouse monoclonal antibodies (XM210; Abcam) were used as the anti-cortisol antibodies, and HBS-EP buffer (Biacore) as the running buffer.

Figure 15:
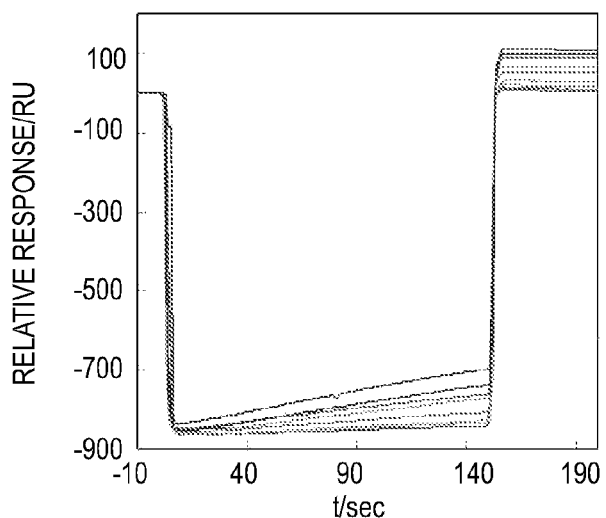
FIG. 15 is a diagram representing SPR curves obtained from a standard cortisol solution (Example 1).

FIG. 15 represents the SPR curve obtained for the cortisol solution of each concentration. In the figure, the peak shift of about 850 RU (Resonance Unit) occurring at 0 sec is the bulk effect due to the switching from the running buffer to the standard sample solution. The bulk effect disappears at 150 sec by the switching of the standard sample solution to the running buffer.

From 0 to 150 sec, a time-course increase of RU was observed as a result of the binding of the anti-cortisol antibodies to the cortisol immobilized on the surface of the sensor substrate. The RU increase was smaller in higher concentrations of the standard cortisol solution, and larger in lower concentrations of the standard cortisol solution. This suggests that the indirect competitive SPR has functioned according to its measurement principle.

Figure 16A:
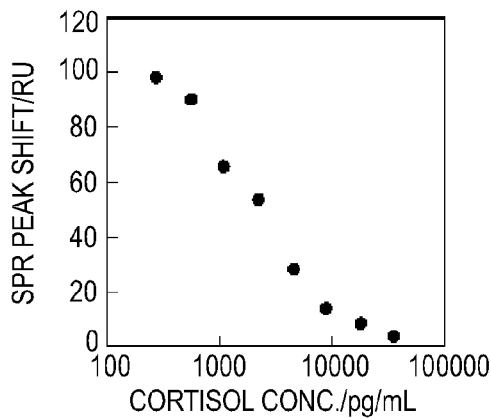
FIGS. 16A and 16B are diagrams representing a plot of SPR shifts, and a standard curve obtained from a standard cortisol solution (Example 1).

FIG. 16A is a graph obtained by calculating RU 60 seconds after the end of the injection in comparison to the baseline.

(3) Sample Measurement

Figure 16B:
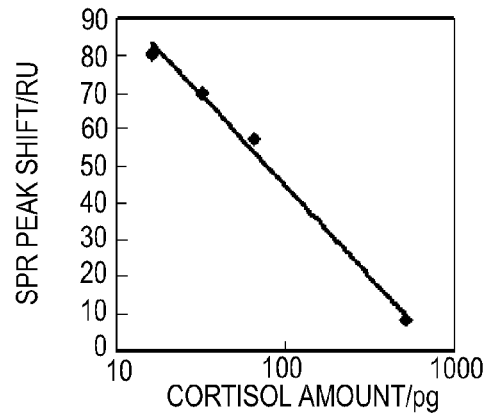

40 µL of the sample prepared in Example 1 was thoroughly mixed with 40 µL of an anti-cortisol antibody solution to run a binding reaction. After the binding reaction, 40 µL of the standard sample solution was injected at 20 µL/min, at 25° C. The standard curve created under the same conditions is represented in FIG. 16B.

Table 2 presents cortisol levels (pg) calculated for eight subjects (subjects a to h) using the standard curve. Several ten picograms of cortisol were detected in each subject.

TABLE 2

| Subject | Response/RU | Cortisol/pg |
|---------|-------------|-------------|
| a | 72.5 | 27.10 |
| b | 91.5 | 11.09 |
| c | 53.8 | 65.33 |
| d | 76.4 | 22.56 |
| e | 74.7 | 24.44 |
| f | 68.3 | 33.02 |
| g | 57.2 | 55.67 |
| h | 47.6 | 87.46 |

Example 2

Quantification of Catecholamines

1. Acquisition of Norepinephrine and L-DOPA from Skin Surface

Norepinephrine and L-DOPA were collected from the skin surface according to (1) the collection method using a microtube described in Section 1 (Acquisition of Cortisol from Skin Surface) of Example 1. In this Example, however, water was used as the solvent, and the contact time for the skin surface was 3 min.

2. Quantification Using High-Performance Liquid Chromatography (HPLC)

40 µL of water contacted to the skin surface (hereinafter, simply "sample") was collected in a vial. 30 µL of the sample was then analyzed by high-performance liquid chromatography (NANOSPACE SI-2, SHISEIDO).

2.5% acetonitrile water was flown at a flow rate of 100 µL/min, using CAPCELLPAK MF Ph-1 (column size 1.5 mm ID×35 mm, column temperature 35° C., SHISEIDO) as a pretreatment column. CAPCELLPAK C18 MGII S5 (column size 2.0 mm I.D.×250 mm, column temperature 40° C., SHISEIDO) was used as an analytical column.

Mobile phase: AB=90/10 ((A) 1.0 mM sodium octanesulfonate, 0.02 mM EDTA-2Na, 10 mM $KH_2PO_4$, 0.05 vol % $H_3PO_4$, (B) $CH_3CN$)

Flow rate: 200 µL

Injection amount: 2 µL or 5 µL

Figure 17:
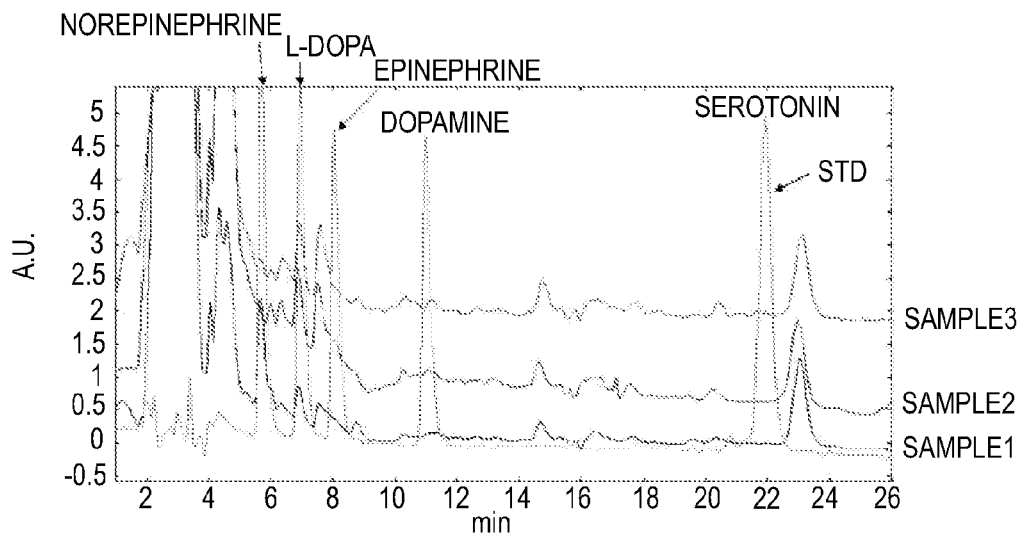
FIG. 17 is a diagram representing the results of the measurement of norepinephrine level and L-DOPA level using high-performance liquid chromatography (HPLC) (Example 2).

The measurement results are presented in FIG. 17. Sample-1 represents a chromatogram obtained from a concentrated solution of the sample. Sample-2 and Sample-3 represent chromatograms obtained from unconcentrated samples. STD represents a chromatogram obtained from a standard solution (a solution containing norepinephrine, epinephrine, L-DOPA, dopamine, and serotonin).

While peaks corresponding to norepinephrine and L-DOPA were detected in the chromatograms of Sample-1 to Sample-3, no peaks were detected that corresponded to epinephrine, dopamine, and serotonin.

Table 3 presents the norepinephrine and L-DOPA levels (pg) calculated from the peak area determined based on the baseline, using the standard curve.

TABLE 3

|  | Injection amount | | | |
|---|---|---|---|---|
|  | 2 μl | | 5 μl | |
|  | Norepinephrine | L-DOPA | Norepinephrine | L-DOPA |
| Sample-1 | 7.58 | 2.42 | 19.37 | 7.17 |
| Sample-2 | N.D. | 5.50 | N.D. | 15.68 |
| Sample-3 | N.D. | 5.35 | N.D. | 14.71 |

Norepinephrine was below the detection limit (N.D.) in the unconcentrated Sample-2 and Sample-3, whereas about several to several ten picograms were detected in the concentrated Sample-1. About several to several ten picograms of L-DOPA were quantified in all of Sample-1 to Sample-3. The results thus confirmed that about several to several ten picograms of norepinephrine and L-DOPA could be collected from the skin surface.

Example 3

Quantification of Serotonin

1. Acquisition of Serotonin from Skin Surface

Serotonin was collected from the skin surface according to the method of Example 2.

2. Quantification Using High-Performance Liquid Chromatography (HPLC)

100 μL of water contacted to skin surface (hereinafter, simply "sample") was collected in a vial. 100 μL of the sample was then analyzed by high-performance liquid chromatography (NANOSPACE SI-2, SHISEIDO).

CAPCELL PAK C18 MGII S5 (column size 2.0 mm ID×35 mm, column temperature 40° C., SHISEIDO) was used as a pretreatment column. CAPCELLPAK C18 UG120 S3 (column size 1.5 mm ID×250 mm, column temperature 40° C., SHISEIDO) was used as an analytical column. Mobile phase (AB=87/13 ((A) 4 mM Sodium 1-octanesulfonate, 0.02 mM EDTA-2Na, 5 mM KH2PO4 (pH 3.4); (B) CH3CN)) was fed at a flow rate of 100 μL/min. An electrochemical detector (ECD OX 750 mV (Ag)) was used for the detection.

Figure 18:
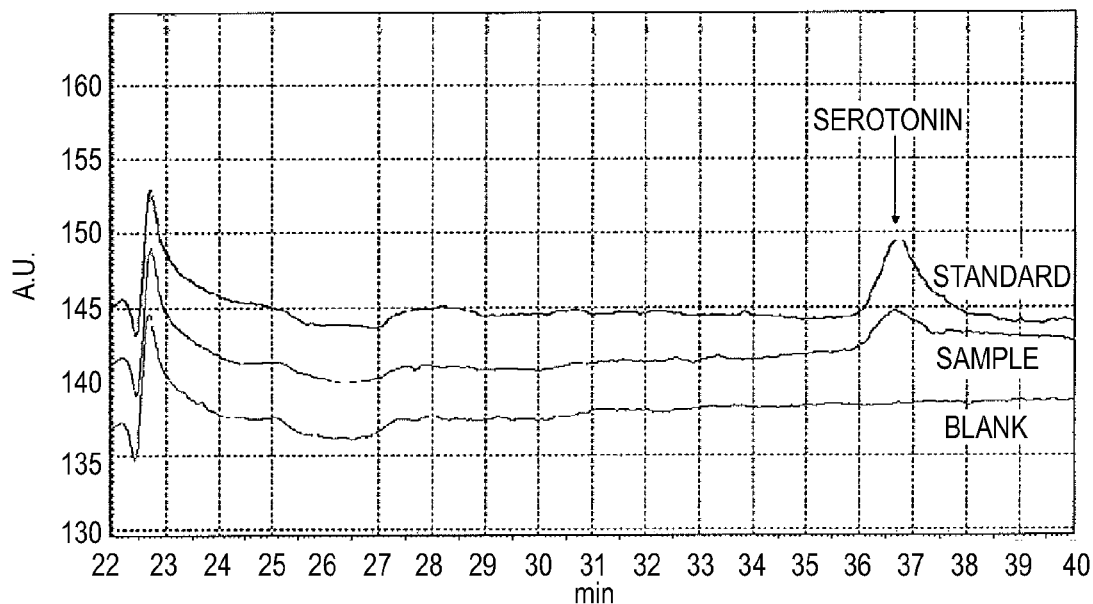
FIG. 18 is a diagram representing the results of the measurement of serotonin level using high-performance liquid chromatography (HPLC) (Example 3).

The measurement results are presented in FIG. 18. "Sample" represents a chromatogram obtained from a concentrated solution (100×) of the sample. "Standard" represents a chromatogram obtained from a 0.1 μM solution of standard serotonin (Wako Pure Chemical Industries, Ltd.).

In the sample and standard serotonin chromatograms, peaks are detected at the elution time of 36 to 38 min. The serotonin concentration calculated from the area in the chromatogram was about 4.4 ng/mL in the 100× concentrated solution of the sample, and about 0.044 ng/mL of serotonin were collected from the skin surface of the index finger.

Example 4

Quantification of Estradiol

1. Acquisition of Estradiol from Skin Surface

Estradiol was collected from skin surface according to the method of Example 2. Estradiol was collected from eight subjects.

2. Quantification Using Enzyme Immunoassay (Enzyme-Linked Immunosorbent Assay: ELISA)

100 μL of water contacted to skin surface (hereinafter, simply "sample") was collected in a vial. 100 μL of the sample was then analyzed using a commercially available ELISA kit (High Sensitivity SALIVARY 17β-ESTRADIOL ENZYME IMMNOAS SAY KIT, SALIMETRICS).

Figure 19:
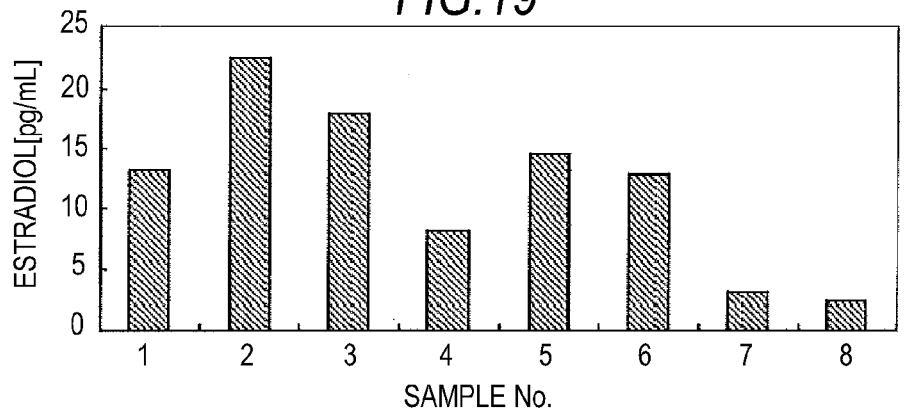
FIG. 19 is a diagram representing the results of the measurement of estradiol level using enzyme immunoassay (ELISA) (Example 4).

A standard curve was created through the measurement of the standard estradiol attached to the kit, and the estradiol concentration in the sample was calculated. The results are presented in FIG. 19. The estradiol concentration was about 2 to 23 pg/ml in each sample. The results thus confirmed that about several to several ten picograms of estradiol could be collected from the skin surface of the index finger.

Example 5

Quantification of Growth Hormone

1. Acquisition of Growth Hormone from Skin Surface

Growth hormone was collected from skin surface according to the method of Example 2. Here, growth hormone was collected from the skin surface of the thumbs of three subjects.

2. Quantification Using Enzyme Immunoassay (ELISA)

100 μL of the sample was collected in a vial, and analyzed using a commercially available ELISA kit (hGH ELISA, Roche).

Figure 20:
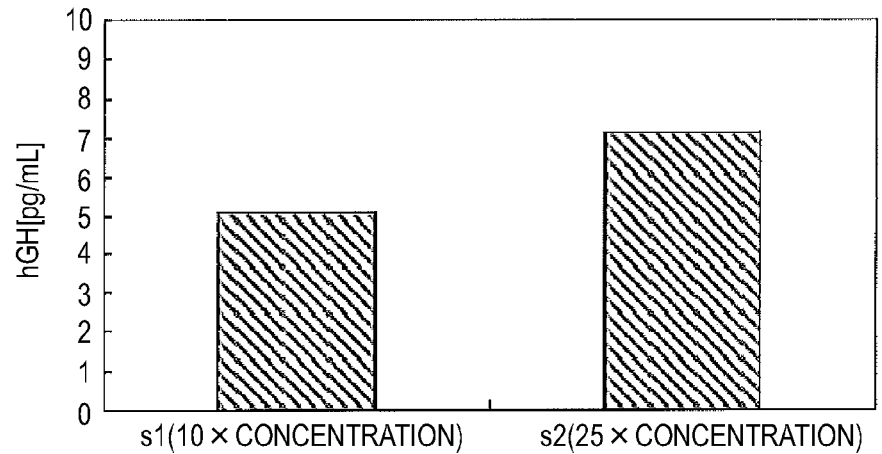
FIG. 20 is a diagram representing the results of the measurement of growth hormone level using enzyme immunoassay (ELISA) (Example 5).

A standard curve was created through the measurement of the standard growth hormone attached to the kit, and the growth hormone concentration in the sample was calculated. The results are presented in FIG. 20. In the figure, s1 is the 10× concentrated solution, and s2 the 25× concentrated solution of the sample. It was possible to collect 0.29 to 0.51 pg/mL of growth hormone from the skin surface of the thumb.

The physiologically active substance collecting device according to the embodiment of the present disclosure can be used to collect a physiologically active substance from a living organism on a steady basis in a convenient and minimally invasive manner. Because the device can acquire accurate biological information based on the quantified value of the acquired physiologically active substance, the present disclosure has use in, for example, biological information sensing in the fields of home healthcare and entertainment such as in games.

It should be understood that various changes and modifications to the presently preferred embodiments described herein will be apparent to those skilled in the art. Such changes and modifications can be made without departing from the spirit and scope and without diminishing its intended advantages. It is therefore intended that such changes and modifications be covered by the appended claims.

The application is claimed as follows:

1. A physiologically active substance collecting device, comprising:
   a collecting section brought into contact with a body surface of a living organism to acquire a physiologically active substance from the body surface;
   one or more channels for sending a solvent to the collecting section, the collecting section having an aperture wherein the solvent flows through the one or more channels to contact the body surface;
   an air sending unit that sends air to the collecting section to selectively introduce the solvent and air into the collecting section
   a lead-out section that drains the solvent that has contacted the body surface at the aperture;
   an absorber that is sent to the lead-out section to absorb and hold the solvent, wherein the absorber that absorbs and holds the solvent is sent to the lead-out section by rotating a core and reeling out the absorber wound around the core; and a drying unit for evaporating and removing the solvent from the absorber absorbing and holding the solvent.

2. The physiologically active substance collecting device according to claim 1, wherein the collecting section includes a collection substrate that includes a first channel that provides a flow path for the solvent, a solvent inlet for the first channel, a solvent outlet for the first channel, and the aperture positioned between the inlet and the outlet of the first channel.

3. The physiologically active substance collecting device according to claim 2, wherein the collection substrate is replaceable from the collecting section.

4. The physiologically active substance collecting device according to claim 2, wherein the collecting section includes an anchor substrate that includes a second channel that provides a flow path for the solvent sent from a solvent tank and a third channel that provides a flow path for the solvent sent to a lead-out section that drains the solvent that has contacted the body surface.

5. The physiologically active substance collecting device according to claim 4, wherein the anchor substrate is anchored to the collecting section.

* * * * *